United States Patent [19]
Garvey et al.

[11] Patent Number: 5,932,538
[45] Date of Patent: Aug. 3, 1999

[54] NITROSATED AND NITROSYLATED α-ADRENERGIC RECEPTOR ANTAGONIST COMPOUNDS, COMPOSITIONS AND THEIR USES

[75] Inventors: David S. Garvey, Dover; Joseph D. Schroeder, Cambridge, both of Mass.; Inigo Saenz de Tejada, Madrid, Spain

[73] Assignee: NitroMed, Inc., Bedford, Mass.

[21] Appl. No.: 08/595,732

[22] Filed: Feb. 2, 1996

[51] Int. Cl.⁶ .................. A01N 43/54; A61K 31/505; A61K 31/13

[52] U.S. Cl. .................. 514/2; 514/258; 514/259; 514/260; 514/280; 514/423; 514/562; 514/644; 514/645; 514/8; 514/23

[58] Field of Search .................. 514/254, 258–260, 514/280, 423, 562, 644–645, 2, 8, 23

[56] References Cited

U.S. PATENT DOCUMENTS

| | | | |
|---|---|---|---|
| 5,236,904 | 8/1993 | Gerstenberg et al. | 514/12 |
| 5,380,758 | 1/1995 | Stamler et al. | 514/562 |
| 5,447,912 | 9/1995 | Gerstenberg et al. | 514/12 |
| 5,474,535 | 12/1995 | Place et al. | 604/60 |
| 5,565,466 | 10/1996 | Gioco et al. | 514/280 |
| 5,567,706 | 10/1996 | Gavras | 514/280 |
| 5,574,068 | 11/1996 | Stamler et al. | 514/562 |
| 5,593,876 | 1/1997 | Stamler et al. | 435/188 |
| 5,612,314 | 3/1997 | Stamler et al. | 514/13 |
| 5,646,181 | 7/1997 | Fung et al. | 514/506 |
| 5,648,393 | 7/1997 | Stamler et al. | 514/562 |

FOREIGN PATENT DOCUMENTS

| | | |
|---|---|---|
| 0346297 | 12/1989 | European Pat. Off. . |
| 0432199 | 6/1991 | European Pat. Off. . |

OTHER PUBLICATIONS

Miyamoto et al, Arzneim–Forsh Drug/Res 41(II) No. 12 (1991) pp. 1216–1221.
Gould et al, *Angiology*, 32(9):595–600 (1981).
Krane et al, *New England Journal Of Medicine*, 321(24):1648–1659 (1989).

*Primary Examiner*—Cecilia J. Tsang
*Assistant Examiner*—Bennett Celsa
*Attorney, Agent, or Firm*—Hale and Dorr LLP

[57] ABSTRACT

Disclosed are nitrosated and nitrosylated α-adrenergic receptor antagonists, compositions of an α-adrenergic receptor antagonist (α-antagonist), which can optionally be substituted with at least one NO or $NO_2$ moiety, and a compound that donates, transfers or releases nitric oxide as a charged species, i.e., nitrosonium ($NO^+$) or nitroxyl ($NO^-$), or as the neutral species, nitric oxide (NO●); and uses for each of them in treating human male impotence or erectile dysfunction.

20 Claims, 5 Drawing Sheets

NITROSATED AND NITROSYLATED α-ADRENERGIC RECEPTOR ANTAGONIST COMPOUNDS, COMPOSITIONS AND THEIR USES

FIELD OF THE INVENTION

This invention generally relates to α-adrenergic receptor antagonists, compositions containing them and their use in treating human male impotence.

BACKGROUND OF THE INVENTION

Erectile dysfunction or impotence is a widespread disorder that is thought to affect about ten to fifeteen percent of adult men. Some pharmacological methods of treatment are available. Such methods, however, have not proven to be highly satisfactory or without potentially severe side-effects. Papaverine is now widely used to treat impotence, although papaverine is ineffective in overcoming impotence due, at least in part, to severe atherosclerosis. Papaverine is effective in cases where the dysfunction is psychogenic or neurogenic and severe atherosclerosis is not involved. Injection of papaverine, a smooth muscle relaxant, or phenoxybenzamine, a non-specific antagonist and hypotensive, into a corpus cavernosum has been found to cause an erection sufficient for vaginal penetration however, these treatments are not without the serious and often painful side effect of priapisim. Also, in cases where severe atherosclerosis is not a cause of the dysfunction, intracavernosal injection of phentolamine, an α-adrenergic antagonist, is used. As an alternative or, in some cases, blockade, prostaglandin E1 (PGE1) has been administered via intracavernosal injection. A major side effect frequently associated with intracorprally delivered PGE1 is penile pain and burning. Thus, there is a need for treatments of human male impotence without the undesirable side effects of those agents currently used.

SUMMARY OF THE INVENTION

Nitric oxide (NO) and NO donors have been recognized as mediators of nonvascular smooth muscle relaxation. This effect includes the dilation of the corpus cavernosum smooth muscle, an event involved in the penile erection process. However, the effects of such compounds together with α-adrenergic receptor antagonists or the modifications of α-adrenergic receptor antagonists to be directly or indirectly linked with a nitric oxide adduct have not been investigated.

In the process of arriving at the present invention it was recognized that the risk of toxicities and adverse effects that are associated with high doses of α-adrenergic receptor antagonists can be avoided by the use of such α-adrenergic receptor antagonists when nitrosated or nitrosylated or when administered in conjunction with compounds that donate, release or transfer nitric oxide. Such toxicities and adverse effects include postural hypotension, reflex tachycardia and other arrythmias, syncope and, with respect to the ergot alkaloids, nausea and vomiting and, upon prolonged or excessive administration, vascular insufficiency and gangrene of the extremities. The α-adrenergic receptor antagonists and compounds that donate, release or transfer nitric oxide work together to permit the same efficacy with lower doses of the α-adrenergic receptor antagonists.

Accordingly, in one aspect the invention provides novel nitrosated and nitrosylated α-adrenergic receptor antagonists ($NO_n$-α-antagonists) wherein n is 1 or 2. The α-adrenergic antagonist can be nitrosylated or nitrosated through sites such as oxygen (hydroxyl condensation), sulfur (sulfhydryl condensation), carbon and nitrogen. The invention also provides compositions comprising such compounds in a pharmaceutically acceptable carrier. pharmaceutically acceptable carrier.

In another aspect the invention provides a composition comprising a therapeutically effective amount of an α-adrenergic receptor antagonist (α-antagonist), which can optionally be substituted with at least one NO or $NO_2$ moiety, and a compound that donates, transfers or releases nitric oxide as a charged species, i.e., nitrosonium ($NO^+$) or nitroxyl ($NO^-$), or as the neutral species, nitric oxide (NO●), preferably in a one to ten fold molar excess. The invention also provides compositions comprising such compounds in a pharmaceutically acceptable carrier. The α-adrenergic receptor antagonist used in the composition can be those described above and others which are known and can alternatively be such α-antagonists which have been nitrosated or nitrosylated in accordance with the invention.

In another aspect, the invention provides a method for treating male impotence in humans which comprises administering to an individual in need thereof a therapeutically effective amount of a nitrosated or nitrosylated α-antagonist.

In another aspect, the invention provides a method for treating male impotence in humans which comprises administering to an individual in need thereof a composition comprising a therapeutically effective amount of an α-antagonist which can optionally be substituted with at least one NO or $NO_2$ moiety, and a compound that donates, transfers or releases nitric oxide as a charged species, i.e., nitrosonium ($NO^+$) or nitroxyl ($NO^-$), or as the neutral species, nitric oxide (NO●). The α-antagonist or α-antagonist directly or indirectly linked to at least one NO or $NO_2$ group, and nitric oxide donor can be administered separately or as components of the same composition.

DETAILED DESCRIPTION OF THE INVENTION

Figure 1:
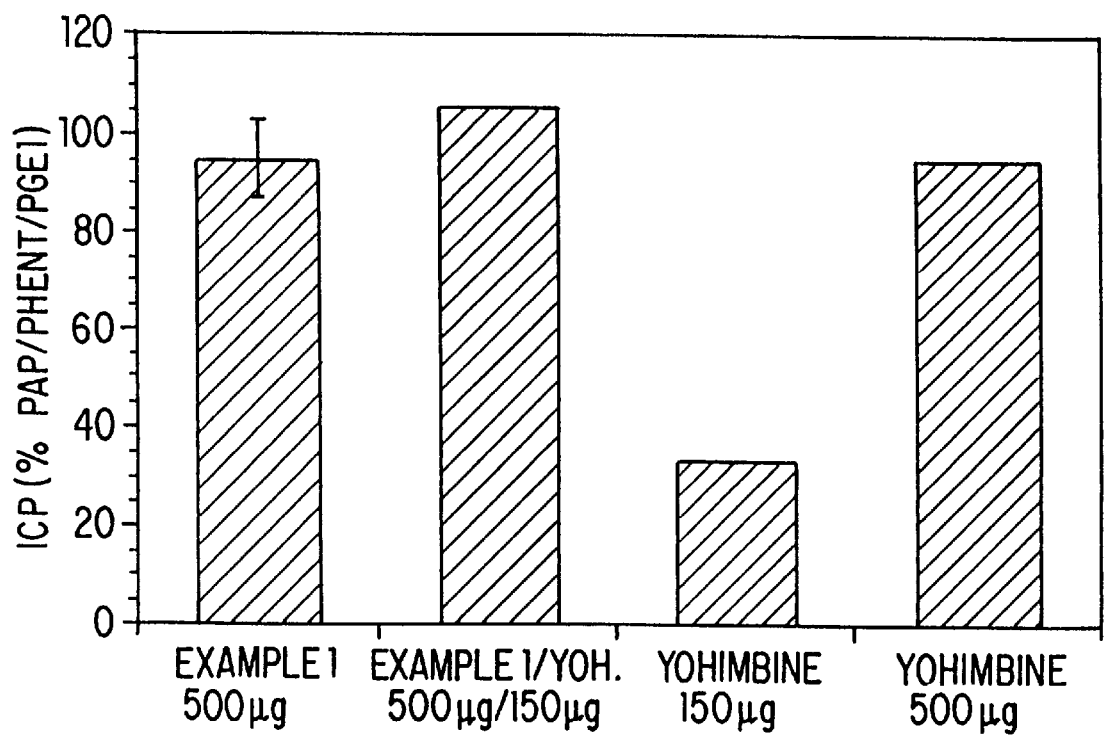
FIG. 1 shows the percent peak erectile response in vivo compared to that produced by 150μl of pap/phent/PGE1 (30 mg/ml: 1 mg/ml: 10 μg/ml) in the anesthetized rabbit following the intracavernosal injection of 150 μl of yohimbine (150 μg, 500 μg), Example 1 (500 μg), and a combination of yohimbine (150 μg) and Example 1 (500 μg). The ordinate is the percent response of intracavernosal pressure relative to that produced by pap/phent/PGE1 and the abscissa indicates the various drugs given.

The term "lower alkyl" as used herein refers to branched or straight chain alkyl groups comprising one to ten carbon atoms, including methyl, ethyl, propyl, isopropyl, n-butyl, t-butyl, neopentyl and the like.

The term "alkoxy" as used herein refers to $R_{50}O$-wherein $R_{50}$ is lower alkyl as defined above. Representative examples of alkoxy groups include methoxy, ethoxy, t-butoxy and the like.

The term "alkoxyalkyl" as used herein refers to an alkoxy group as previously defined appended to an alkyl group as previously defined. Examples of alkoxyalkyl include, but are not limited to, methoxymethyl, methoxyethyl, isopropoxymethyl and the like.

The term "hydroxy" as used herein refers to —OH.

The term "hydroxyalkyl" as used herein refers to a hydroxy group as previously defined appended to an alkyl group as previously defined.

The term "alkenyl" as used herein refers to a branched or straight chain $C_2$–$C_{10}$ hydrocarbon which also comprises one or more carbon-carbon double bonds.

The term "amino" as used herein refers to —$NH_2$.

The term "nitrate" as used herein refers to —O—$NO_2$.

The term "alkylamino" as used herein refers to $R_{11}NH$— wherein $R_{11}$ is a lower alkyl group, for example, methylamino, ethylamino, butylamino, and the like.

The term "dialkylamino" as used herein refers to $R_{12}R_{13}N$— wherein $R_2$ and $R_{13}$ are independently selected from lower alkyl, for example dimethylamino, diethylamino, methyl propylamino and the like.

The term "nitro" as used herein refers to the group —$NO_2$ and "nitrosated" refers to compounds that have been substituted therewith.

The term "nitroso" as used herein refers to the group —NO and "nitrosylated" refers to compounds that have been substituted therewith.

The term "aryl" as used herein refers to a mono- or bicyclic carbocyclic ring system having one or two aromatic rings including, but not limited to, phenyl, naphthyl, tetrahydronaphthyl, indanyl, indenyl, and the like. Aryl groups (including bicyclic aryl groups) can be unsubstituted or substituted with one, two or three substituents independently selected from loweralkyl, haloalkyl, alkoxy, amino, alkylamino, dialkylamino, hydroxy, halo, and nitro. In addition, substituted aryl groups include tetrafluorophenyl and pentafluorophenyl.

The term "arylalkyl" as used herein refers to a lower alkyl radical to which is appended an aryl group. Representative arylalkyl groups include benzyl, phenylethyl, hydroxybenzyl, fluorobenzyl, fluorophenylethyl and the like.

The term "cycloalkyl" as used herein refers to an alicyclic group comprising from 3 to 7 carbon atoms including, but not limited to, cyclopropyl, cyclobutyl, cyclopentyl, cyclohexyl and the like.

The term "halogen" or "halo" as used herein refers to I, Br, Cl, or F. The term "haloalkyl" as used herein refers to a lower alkyl radical, as defined above, bearing at least one halogen substituent, for example, chloromethyl, fluoroethyl or trifluoromethyl and the like.

The term "heteroaryl" as used herein refers to a mono- or bi- cyclic ring system containing one or two aromatic rings and containing at least one nitrogen, oxygen, or sulfur atom in an aromatic ring. Heteroaryl groups (including bicyclic heteroaryl groups) can be unsubstituted or substituted with one, two or three substituents independently selected from lower alkyl, haloalkyl, alkoxy, amino, alkylamino, dialkylamino, hydroxy, halo and nitro. Examples of heteroaryl groups include but are not limited to pyridine, pyrazine, pyrimidine, pyridazine, pyrazole, triazole, thiazole, isothiazole, benzothiazole, benzoxazole, thiadiazole, oxazole, pyrrole, imidazole and isoxazole.

The term "heterocyclic ring" refers to any 3-, 4-, 5-, 6-, or 7-membered nonaromatic ring containing at least one nitrogen atom, oxygen, or sulfur atom which is bonded to an atom which is not part of the heterocyclic ring.

The term "arylheterocyclic ring" as used herein refers to a bi- or tricyclic ring comprised of an aryl ring as previously defined appended via two adjacent carbons of the aryl group to a heterocyclic ring as previously defined.

The term "heterocyclic compounds" herein refers to mono and polycyclic compounds containing at least one heteroaryl or heterocyclic ring.

Compounds of the invention which have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the present invention anticipates and includes within its scope all such isomers and mixtures thereof.

The α-adrenergic receptor antagonists that are nitrosated or nitrosylated in accordance with the invention and/or are included in the compositions of the invention can be any of those known to the art, including those exemplified below. Structurally, the α-antagonists can generally be categorized as haloalkylamines, imidazolines, quinozolines, indole derivatives, phenoxypropanolamines, alcohols, alkaloids, amines, piperizines and piperidines.

The first group of α-antagonists are the haloalkylamines that block $α_1$- and $α_2$-adrenergic receptors irreversibly. Included in this group are, for example, phenoxybenzamine and dibenamine. Phenoxybenzamine is used in the treatment of pheochromocytomas, tumors of the adrenal medulla and sympathetic neurons that secrete catecholamines into the circulation. It controls episodes of severe hypertension and minimizes other adverse effects of catecholamines such as contraction of plasma volume and injury of the myocardium.

Another group of such α-antagonists are the imidazolines. These include phentolamine and tolazoline. Phentolamine has similar affinity for $α_1$ and $α_2$ receptors. Phentolamine is used in short-term control of hypertension in patients with pheochromocytoma and direct, intracavernous injection of phentolamine (usually in combination with papaverine) has been proposed as a treatment for male sexual dysfunction. Tolazoline is used in the treatment of persistent pulmonary hypertension in neonates. Others include idazoxan, deriglidole, RX 821002, BRL 44408 and BRL 44409 (see *Eur. J. Pharm.,* 168:381, 1989)

Another group of α-antagonist compounds that are contemplated are the quinazolines. These include, for example, prazosine, a very potent and selective $a_1$ adrenergic antagonist, terazosin, doxazosin, alfuzosin, bunazosin, ketanserin, trimazosin and abanoquil. This group of compounds is principally used in the treatment of primary systemic hypertension and also in the treatment of congestive heart failure.

Another class of such α-adrenergic blocking agents are indole derivatives. These include, for example, carvedilol and BAM 1303.

Another class of such α-adrenergic blocking agents are alcohols. These include, for example, labetelol and ifenprodil.

Another class of such α-adrenergic blocking agents are alkaloids. These include, for example, "ergotoxine," which is a mixture of three alkaloids, i.e., ergocornine, ergocristine and ergocryptine. Both natural and dihydrogenated peptide alkaloids produce α-adrenergic blockade. The principal uses are to stimulate contraction of the uterus postpartum and to relieve the pain of migraine headaches. Another indole alkaloid is yohimbine. This compound is a competitive antagonist that is selective for $\alpha_2$-adrenergic receptors. In humans, it has been observed to increase blood pressure and heart rate and has been used in the treatment of male sexual dysfunction. Other alkaloid α-blockers include rauwolscine, corynathine, raubascine, tetrahydroalstonine, apoyohimbine, akuammigine, β-yohimbine, yohimbol, pseudoyohimbine and epi-3α-cyohimbine.

Another class of such α-adrenergic blocking agents are amines. These include, for example, tamsulosin, benoxathian, atipamezole, BE 2254, WB 4101 and HU-723.

Another class of such α-adrenergic blocking agents are piperizines. These include, for example, naftopil and saterinone.

Another class of such α-adrenergic blocking agents are piperidines. These include, for example, haloperidol.

Each of the above contemplated α-antagonists is described more fully in the literature, such as in Goodman and Gilman, The Pharmacological Basis of Therapeutics (8th Edition), McGraw-Hill, 1990, Pgs. 221–243.

One embodiment of this aspect includes substituted compounds of the formula:

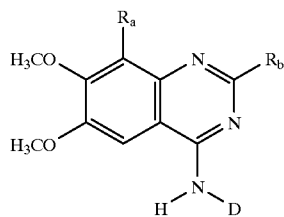

I.

wherein, $R_a$ is selected from hydrogen or alkoxy;

$R_b$ is selected from (i)

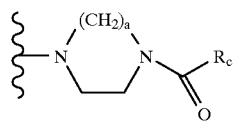

(ii)

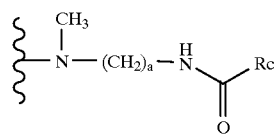

(iii)

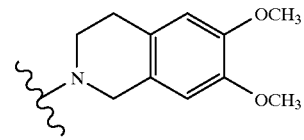

wherein a is an integer of 2 or 3;

$R_c$ is selected from heteroaryl, heterocyclic ring, lower alkyl, hydroxyalkyl, and arylheterocyclic ring;

D is selected from (i) —NO; (ii) —NO$_2$; (iii) —C($R_d$)—O—C(O)—Y—[C($R_e$)($R_f$)]$_p$—T—Q in which $R_d$ is hydrogen, lower alkyl, cycloalkyl, aryl or heteroaryl, Y is oxygen, sulfur, or NR$_i$ in which $R_i$ is hydrogen or lower alkyl, $R_e$ and $R_f$ are independently selected from hydrogen, lower alkyl, cycloalkyl, aryl, heteroaryl, arylalkyl, alkylamino, dialkylamino or taken together are carbonyl, cycloalkyl or bridged cycloalkyl, p is an integer from 1 to 6, T is a covalent bond, oxygen, sulfur or nitrogen and Q is selected from —NO or —NO$_2$; (iv)—(CO)—T$^1$—[C($R_e$)($R_f$)]$_p$—T$^2$—Q wherein T$^1$ and T$^2$ are independently selected from T and $R_e$, $R_f$, p, and T are defined as above; (v) —C(O)—T[C($R_y$)($R_z$)]$_p$ wherein $R_y$ and $R_z$ are independently selected from —T$^1$—[C($R_e$)($R_f$)]$_p$—G—[C($R_e$)($R_f$)]$_p$—T$^2$—Q wherein G is (i) a covalent bond; (ii) —T—C(O)—; (iii) —C(O)—T; and wherein $R_d$, $R_e$, $R_f$, p, Q and T are as defined above.

Another embodiment of this aspect is substituted compounds of the formula:

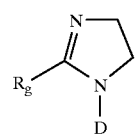

II.

wherein, $R_g$ is selected from:

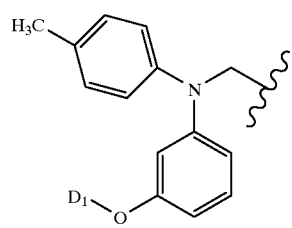

(i)

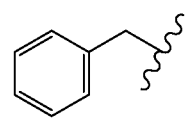

(ii)

(iii)
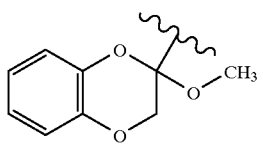

(iv)
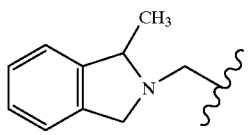

(v)
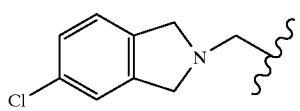

(vi)
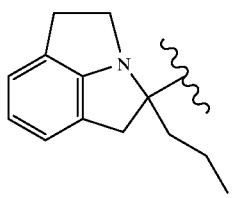

wherein $D_1$ is selected from hydrogen or D wherein D is as defined above.

Another embodiment of this aspect includes substituted compounds of the formula:

III

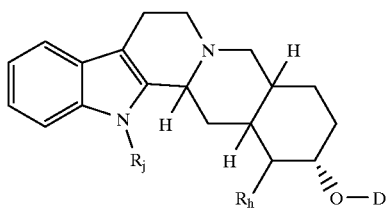

wherein $R_h$ is selected from hydrogen, —C(O)—$OR_d$ or —C(O)—X wherein X is (1) —Y—[C($R_e$)($R_f$)]$_p$—G—[C($R_e$)($R_f$)]$_p$—T—Q; wherein G is (i) a covalent bond; (ii) —T—C(O)—; (iii) —C(O)—T; (iv) —C(Y—C(O)—$R_m$)— wherein $R_m$ is heteroaryl or heterocyclic ring; and in which Y, $R_d$, $R_e$, $R_f$, p, Q and T are as defined above; or (2)

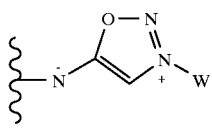

in which W is a heterocyclic ring or $NR_iR'_i$ wherein $R_i$ and $R'_i$ are independently selected from lower alkyl, aryl or alkenyl; and wherein Rj is selected from —D or —(O)$CR_d$ wherein D and $R_d$ are as defined above.

Another embodiment of this aspect includes substituted compounds of the formula:

IV.

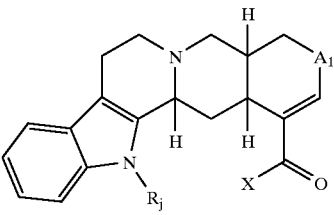

wherein, $A_1$ is oxygen or methylene and X and $R_j$ are as defined above.

Another embodiment of this aspect includes substituted compounds of the formula:

V.

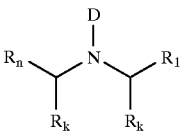

wherein, $R_k$ is selected from hydrogen or lower alkyl;

and wherein $R_l$ is selected from:

(i)
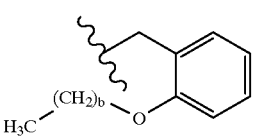

(ii)
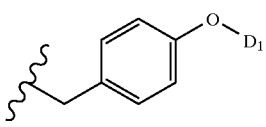

(iii)
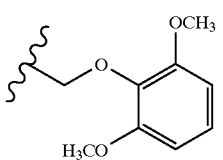

(iv)
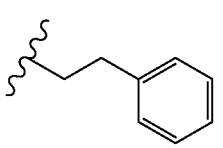

wherein b is an integer of 0 or 1; $D_1$ is as defined above; and $R_n$ is selected from:

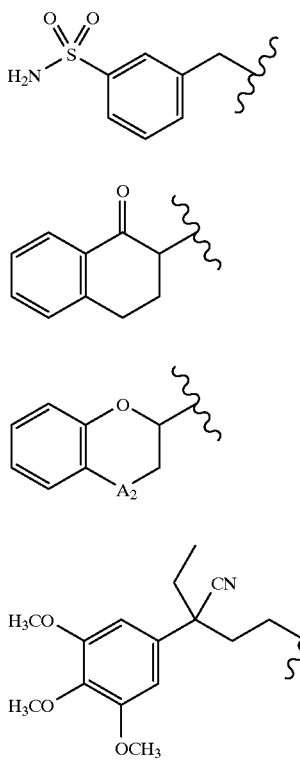

wherein $A_2$ is oxygen or sulfur.

Another embodiment of this aspect includes substituted compounds of the formula:

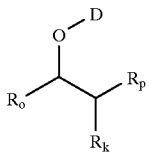

wherein $R_o$ is selected from:

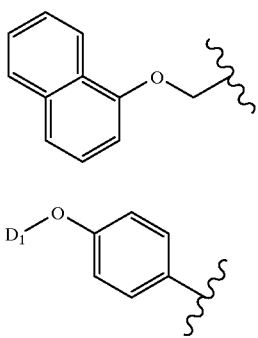

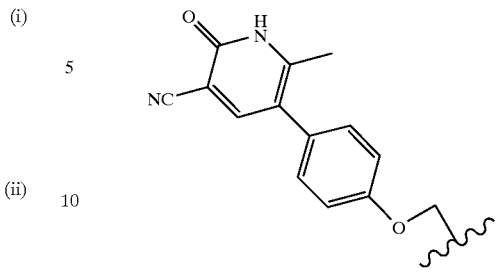

and $R_p$ is selected from:

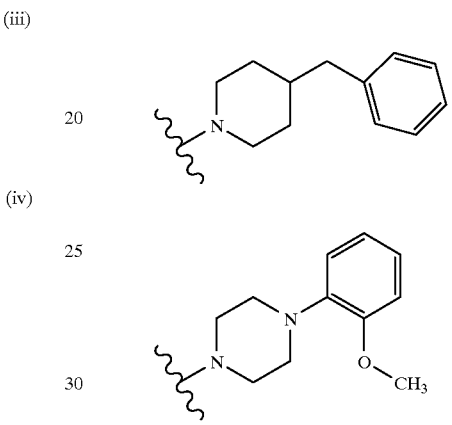

and $R_k$ and D are as defined above.

Another embodiment of this aspect includes substituted compounds of the formula:

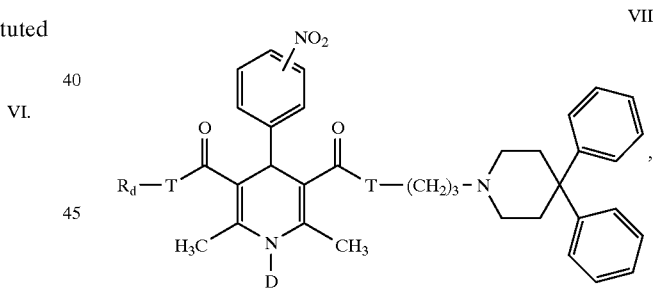

wherein $R_d$, T and D are defined as above.

The present invention also relates to processes for preparing the compounds of formula (I), (II), (III), (IV), (V), (VI) or (VII) and to the intermediates useful in such processes.

Some of the nitrosated and nitrosylated α-antagonists of the present invention may be synthesized as shown in reaction Schemes I through XVIII presented below, in which $R_a$, $R_b$, $R_c$, $R_d$, $R_e$, $R_f$, $R_g$, $R_h$, $R_i$, $R_t$, $R_j$, $R_k$, $R_l$, $R_m$, $R_n$, $R_o$, $R_p$, $A_1$, $A_2$, a, n, W and X are as defined above or as depicted in the reaction schemes for formulas I, II, III, IV, V, VI or VII. $P^1$ is an oxygen protecting group and $P^2$ is a sulfur protecting group. The reactions are performed in solvents appropriate to the reagents and materials employed are suitable for the transformations being effected. It is understood by those skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to skilled practitioners in the art. The use of sulfur and oxygen protecting groups is well known in the art for protecting thiol and alcohol groups against undesirable reactions during a synthetic procedure and many such protecting groups are known, c.f., T. H. Greene and P. G. M. Wuts, *Protective Groups in Organic Synthesis*, John Wiley & Sons, New York (1991).

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Nitroso compounds of formula (I) wherein $R_a$, $R_b$, $R_e$, $R_f$, and p are as defined above and an O-nitrosylated amide is representative of the D group as defined above may be prepared according to Scheme I. The amine group of the quinazoline of the formula 1 is converted to the amide of the formula 2 wherein p, $R_e$ and $R_f$ are as defined above by reaction with an appropriate protected alcohol containing activated acylating agent wherein $P^1$ is as defined above. Preferred methods for the formation of amides are reacting the amine with the preformed acid chloride or symmetrical anhydride of the protected alcohol-containing acid. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosium tetrafluoroborate in a suitable anhydrous solvent such as dichloromethane, THF, DMF, or acetonitrile with or without an amine base such as pyridine or triethylamine affords the compound of the formula IA.

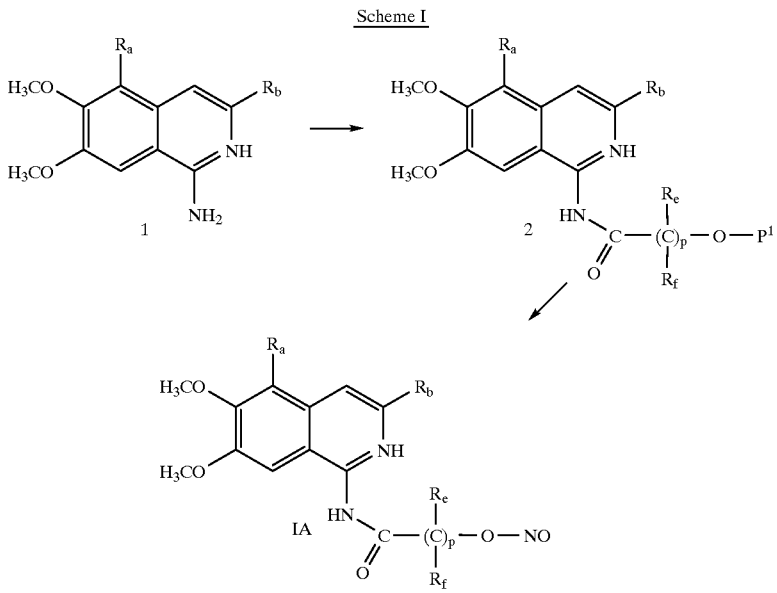

Scheme I

Nitroso compounds of formula (I) wherein $R_a$, $R_b$, $R_e$, $R_f$, and p are defined as above and an S-nitrosylated amide is representative of the D group as defined above may be prepared according to Scheme II. The amine group of the quinazoline of the formula 1 is converted to the amide of the formula 3 wherein p, $R_e$ and $R_f$ are defined as above by reaction with an appropriate protected thiol-containing activated acylating agent wherein $P^2$ is as defined above. Preferred methods for the formation of amides are reacting the amine with the preformed acid chloride or symmetrical anhydride of the protected thiol containing acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a S-triphenylmethyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methyene chloride, THF, DMF, or acetonitrile with or without an amine base such as pyridine or triethylamine affords the compound of the formula IB. Alternatively, treatment of compound 3 with a stoichiometric quantity of sodium nitrite in aqueous acid affords the compound of the formula IB.

dazoline group of the formula 4 is converted to the acyl imidazoline of the formula 5 wherein p, $R_e$ and $R_f$ are defined as above by reaction with an appropriate protected alcohol containing activated acylating agent wherein $P^1$ is as

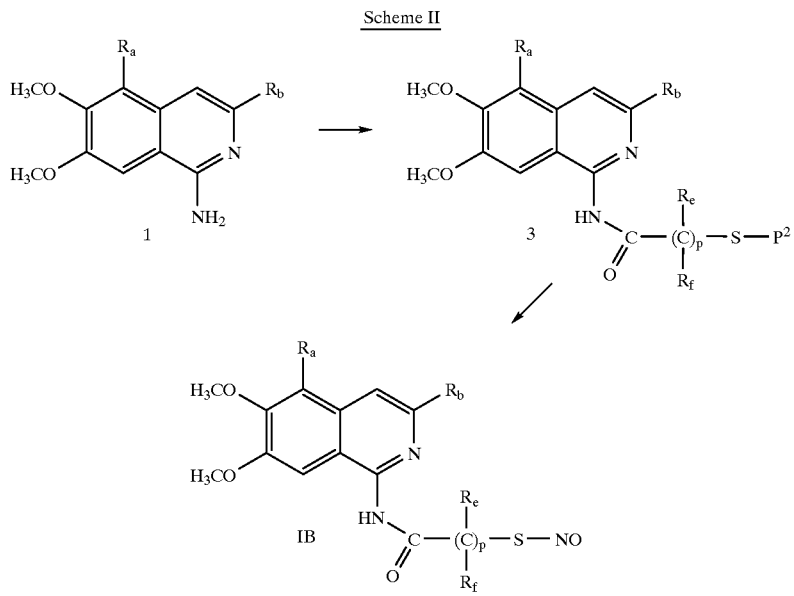

Scheme II

Nitro compounds of formula (I) wherein $R_a$, $R_b$, $R_e$, $R_f$, and p are defined as above and an O-nitrosated amide is representative of the D group as defined above may be prepared according to Scheme III. The amine group of the quinazoline of the formula 1 is converted to the amide of the formula IC wherein p, $R_e$ and $R_f$ are defined as above by reaction with an appropriate nitrate containing activated acylating agent. Preferred methods for the formation of amides are reacting the amine with the preformed acid chloride or symmetrical anhydride of the nitrate containing acid to afford the compound of the formula IC.

defined above. Preferred methods for the formation of acyl imidazolines are reacting the imidazoline with the preformed acid chloride or symmetrical anhydride of the protected alcohol containing acid. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosium tetrafluoroborate in a suitable anhydrous solvent such as dichloromethane, THF, DMF, or acetonitrile with or without an amine base such as pyridine or triethylamine affords the compound of the formula IIA.

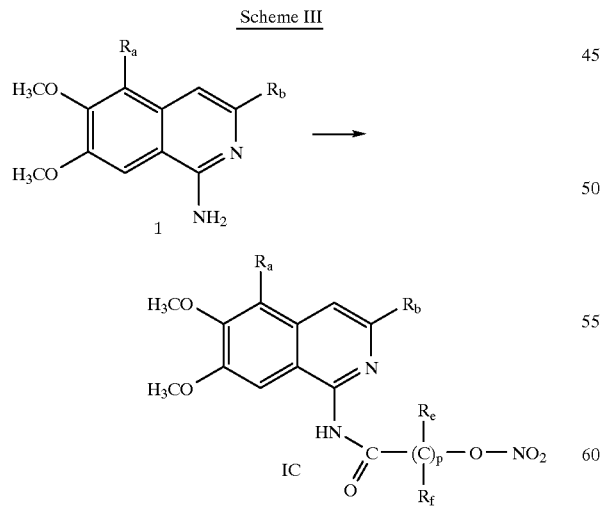

Scheme III

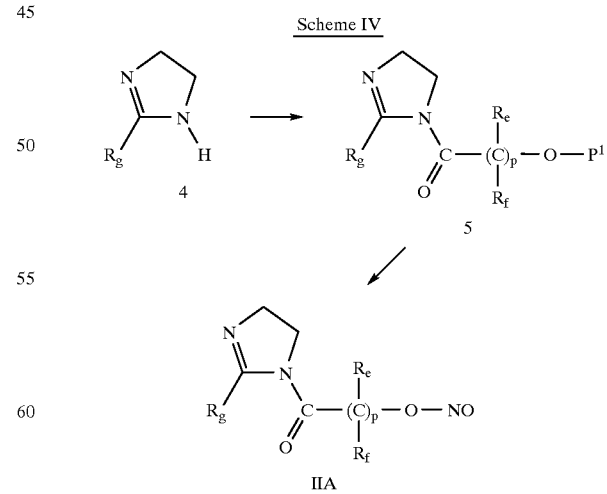

Scheme IV

Nitroso compounds of formula (II) wherein $R_e$, $R_f$, $R_g$, and p are defined as above and an O-nitrosylated acyl imidazoline is representative of the D group as defined above may be prepared according to Scheme IV. The imi- Nitroso compounds of formula (II) wherein $R_e$, $R_f$, $R_g$, and p are defined as above and an S-nitrosylated acyl imidazoline is representative of the D group as defined above may be prepared according to Scheme V. The imidazoline group of the formula 4 is converted to the acyl imidazoline of the formula 6 wherein p, $R_e$ and $R_f$ are defined as above by reaction with an appropriate protected alcohol containing activated acylating agent wherein $P^2$ is as defined above. Preferred methods for the formation of acyl imidazolines are reacting the imidazoline with the preformed acid chloride or symmetrical anhydride of the protected thiol containing acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a S-triphenylmethyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methyene chloride, THF, DMF or acetonitrile with or without an amine base such as pyridine or triethylamine affords the compound of the formula IIB. Alternatively, treatment of compound 6 with a stoichiometric quantity of sodium nitrite in aqueous acid affords the compound of the formula IIB.

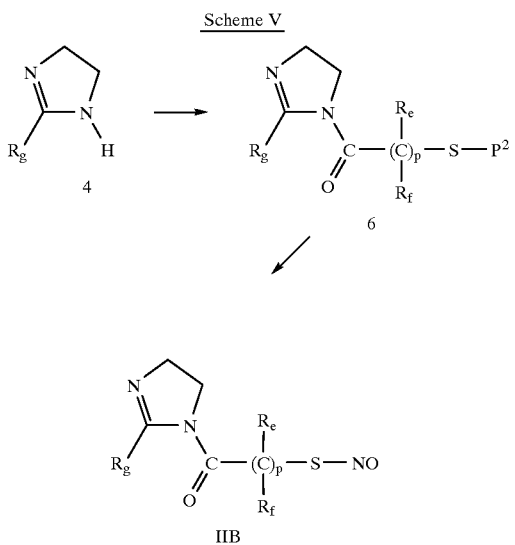

Scheme V

Nitro compounds of formula (II) wherein $R_e$, $R_f$, $R_g$, and p are defined as above and on O-nitrosated acyl imidazoline is representative of the D group as defined above may be prepared according to Scheme VI. The imidazoline group of the formula 4 is converted to the acyl imidazoline of the formula IIC wherein p, $R_e$ and $R_f$ are defined as above by reaction with an appropriate nitrate containing activated acylating agent. Preferred methods for the formation of acyl imidazolines are reacting the amine with the preformed acid chloride or symmetrical anhydride of the nitrate containing acid to afford the compound of the formula IIC.

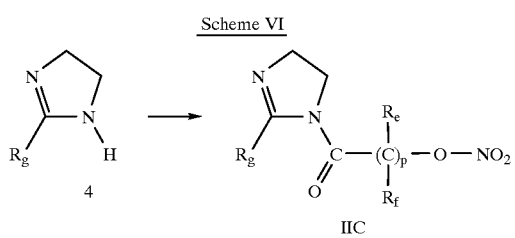

Scheme VI

Nitroso compounds of formula (III) wherein $R_e$, $R_f$, $R_h$, $R_j$, and p are defined as above and an O-nitrosylated ester is representative of the D group as defined above may be prepared according to Scheme VII. The alcohol group of formula 7 is converted to the ester of formula 8 wherein p, $R_e$ and $R_f$ are defined as above by reaction with an appropriate protected alcohol containing activated acylating agent wherein $P^1$ is as defined above. Preferred methods for the formation of esters are reacting the alcohol with the preformed acid chloride or symmetrical anhydride of the protected alcohol containing acid. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosium tetrafluoroborate in a suitable anhydrous solvent such as dichloromethane, THF, DMF, or acetonitrile with or without an amine base such as pyridine or triethylamine affords the compound of the formula IIIA.

Scheme VII

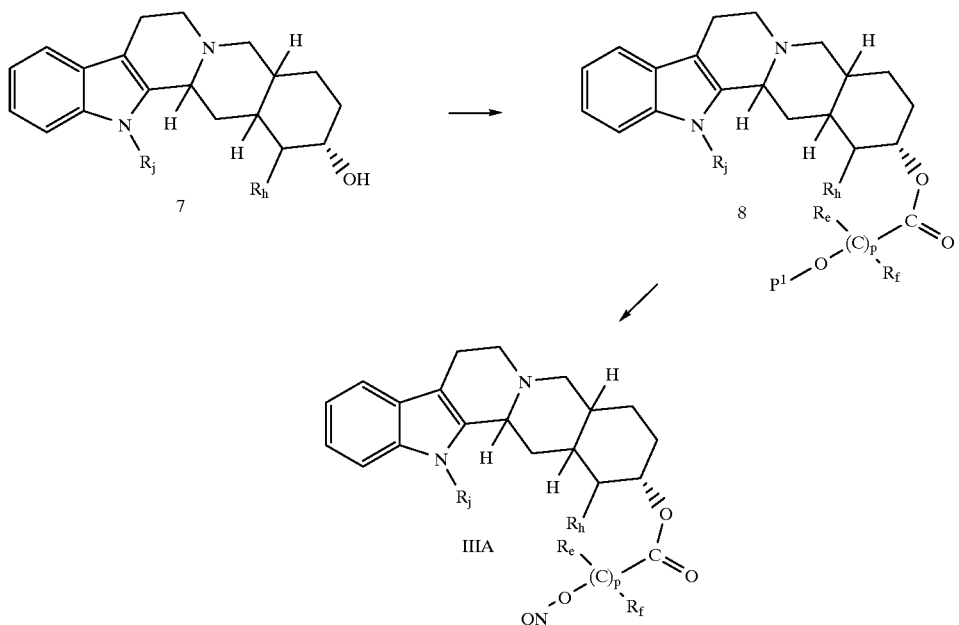

Nitroso compounds of formula (III) wherein $R_e$, $R_f$, $R_h$, $R_j$, and p are defined as above and an S-nitrosylated ester is representative of the D group as defined above may be prepared according to Scheme VIII. The alcohol group of the formula 7 is converted to the ester of the formula 9 wherein p, $R_e$ and $R_f$ are defined as above by reaction with an appropriate protected thiol containing activated acylating agent wherein $P^2$ is as defined above. Preferred methods for the formation of esters are reacting the alcohol with the preformed acid chloride or symmetrical anhydride of the protected thiol containing acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a S-triphenylmethyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methyene chloride, THF, DMF, or acetonitrile with or without an amine base such as pyridine or triethylamine affords the compound of the formula IIIB. Alternatively, treatment of compound 9 with a stoichiometric quantity of sodium nitrite in aqueous acid affords the compound of the formula IIIB.

Scheme VIII

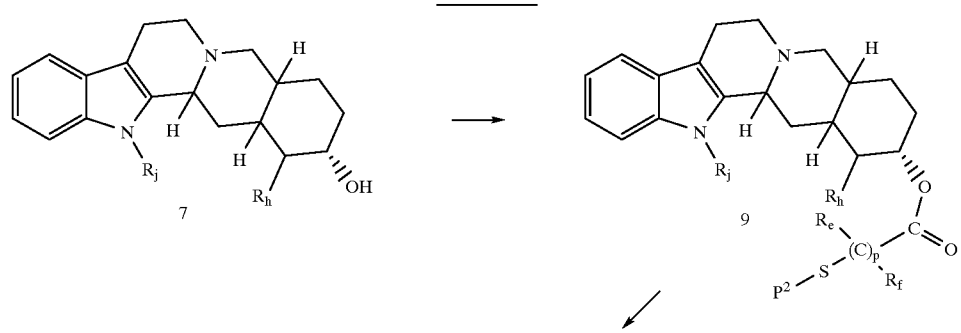

-continued

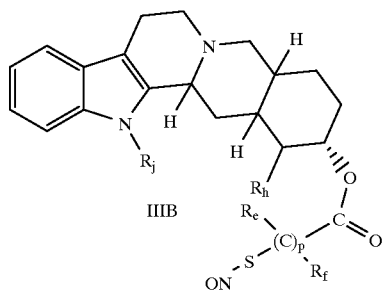

IIIB

Nitro compounds of formula (II) wherein $R_e$, $R_f$, $R_h$, $R_j$, and p are defined as above and an O-nitrosated ester is representative of the D group as defined above may be prepared according to Scheme IX. The alcohol group of the formula 7 is converted to the ester of the formula IIIC wherein p, $R_e$ and $R_f$ are defined as above by reaction with an appropriate nitrate containing activated acylating agent. Preferred methods for the formation of esters are reacting the alcohol with the preformed acid chloride or symmetrical anhydride of the nitrate containing acid to afford a compound of the formula IIIC.

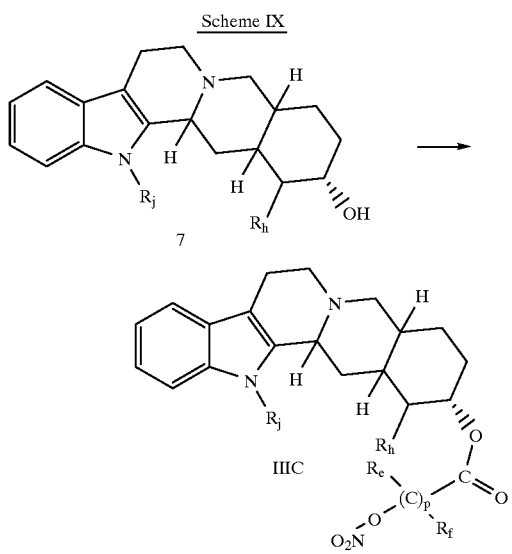

Scheme IX

IIIC

Nitroso compounds of formula (IV) wherein $A_1$, $R_e$, $R_f$, $R_h$, $R_j$, and p are defined as above and an O-nitrosylated ester is representative of the X group as defined above may be prepared according to Scheme X. An acid of the formula 10 is converted into the ester of the formula 11 wherein p, $R_e$, and $R_f$ are defined as above by reaction with an appropriate monoprotected diol. Preferred methods for the preparation of esters are initially forming the mixed anhydride via reaction of 10 with a chloroformate such as isobutylchloroformate in the presence of a non nucleophilic base such as triethylamine in an anhydrous inert solvent such as dichloromethane, diethylether, or THF. The mixed anhydride is then reacted with the monoprotected alcohol preferably in the presence of a condensation catalyst such as 4-dimethylamine pyridine. Alternatively, the acid 10 may be first converted to the acid chloride be treatment with oxalyl chloride in the presence of a catalytic amount of DMF. The acid chloride is then reacted with the monoprotected alcohol preferably in the presence of a condensation catalyst such as 4-dimethylamino- pyridine and a tertiary amine base such as triethyl amine to afford the ester 11. Alternatively, the acid 10 and monoprotected diol may be coupled to afford 11 by treatment with a dehydration agent such as dicyclohexyl-carbodiimide. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosium tetrafluoroborate in a suitable anhydrous solvent such as dichloromethane, THF, DMF, or acetonitrile affords the compound of the formula IVA.

Scheme X

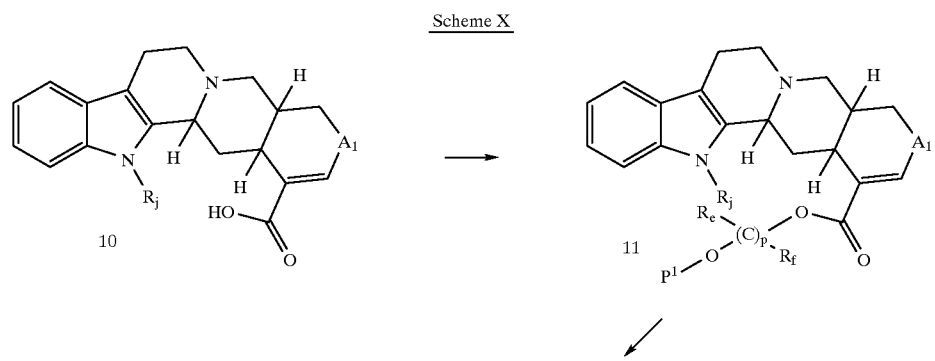

-continued

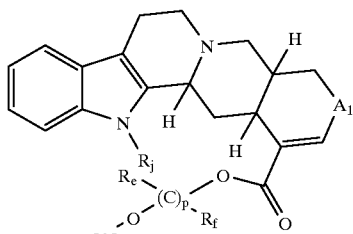

IVA

Nitroso compounds of formula (IV) wherein $A_1$, $R_e$, $R_f$, $R_h$, $R_j$, and p are defined as above and an S-nitrosylated ester is representative of the X group as defined above may be prepared according to Scheme XI. An acid of the formula 10 is converted into the ester of the formula 12 wherein p, $R_e$, and $R_f$ are defined as above and a S-nitrosylated ester is representative of the X group as defined above by reaction with an appropriate protected thiol containing alcohol. Preferred methods for the preparation of esters are initially forming the mixed anhydride via reaction of 10 with a chloroformate such as isobutylchloroformate in the presence of a non nucleophilic base such as triethylamine in an anhydrous inert solvent such as diethylether or THF. The mixed anhydride is then reacted with the thiol containing alcohol preferably in the presence of a condensation catalyst such as 4-dimethylaminopyridine. Alternatively, the acid 10 may be first converted to the acid chloride be treatment with oxalyl chloride in the presence of a catalytic amount of DMF. The acid chloride is then reacted with the monoprotected thiol preferably in the presence of a condensation catalyst such as 4-dimethylamine pyridine and a tertiary amine base such as triethyl amine to afford the ester 12. Alternatively, the acid and thiol containing alcohol may be coupled to afford 12 by treatment with a dehydration agent such as dicyclohexylcarbodiimide. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether, or a S-triphenylmethyl thioether. Deprotection of the thiol moiety (zinc in dilute aqueous acid, triphenylphosphine in water and sodium borohydride are preferred methods for reducing disulfide groups while aqueous base is typically utilized to hydrolyze thiolesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylnethyl thioether group) followed by reaction a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF or acetonitrile with or without an amine base such as pyridine or triethylamine affords the compound of the formula IVB. Alternatively, treatment of compound 12 with a stoichiometric quantity of sodium nitrite in aqueous acid affords the compound of the formula IVB.

Scheme XI

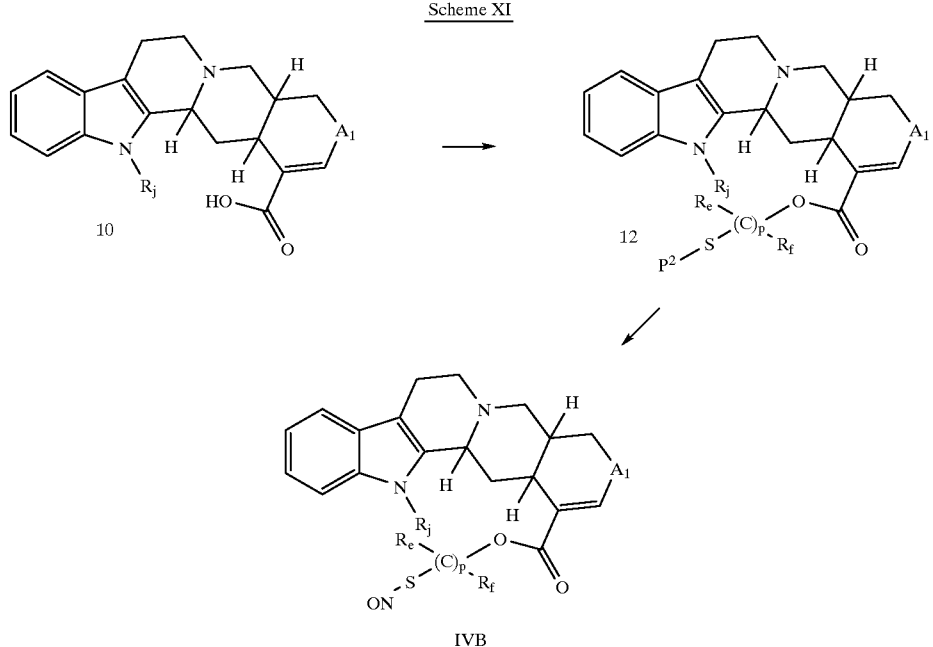

IVB

Nitro compounds of formula (IV) wherein $A_1$, $R_e$, $R_f$, $R_h$, $R_j$, and p are defined as above and an O-nitrosated ester is representative of the X group as defined above may be prepared according to Scheme XII. An acid of the formula 10 is converted into the ester of the formula IVC wherein p, $R_e$, and $R_f$ are defined as above by reaction with an appropriate nitrate containing alcohol. Preferred methods for the preparation of esters are initially forming the mixed anhydride via reaction of 10 with a chloroformate such as isobutylchloroformate in the presence of a non nucleophilic base such as triethylamine in an anhydrous inert solvent such as dichloromethane, diethylether, or THF. The mixed anhydride is then reacted with the nitrate containing alcohol preferably in the presence of a condensation catalyst such as 4-dimethylamino-pyridine. Alternatively, the acid 10 may be first converted to the acid chloride be treatment with oxalyl chloride in the presence of a catalytic amount of DMF. The acid chloride is then reacted with the nitrate containing alcohol preferably in the presence of a condensation catalyst such as 4-dimethylaminopyridine and a tertiary amine base such as triethyl amine to afford the a compound of the formula IVC. Alternatively, the acid 10 and nitrate containing alcohol may be coupled to afford a compound of the formula IVC by treatment with a dehydration agent such as dicyclohexylcarbodiimide.

Scheme XII

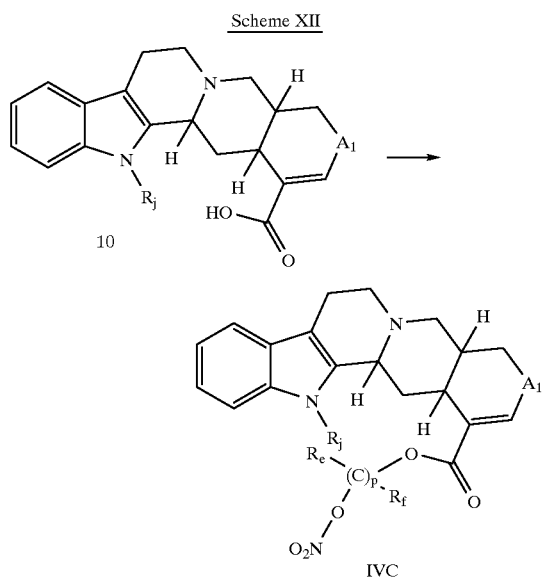

Nitroso compounds of formula (V) wherein $R_e$, $R_f$, $R_k$, $R_l$, $R_n$, and p are defined as above and an O-nitrosylated N-acyloxyalkyl amine is representative of the D group as defined above may be prepared according to Scheme XIII. The amine group of the compound of the formula 13 is converted to the N-acyloxyalkyl amine of the formula 14 wherein p, $R_e$, and $R_f$ are defined as above by reaction with an appropriate protected alcohol containing chloromethyl acyl derivative wherein $P^1$ is as defined above. Preferred methods for the formation of N-acyloxyalkyl amines are reacting the amine with the preformed chloromethyl acyloxyalkyl derivative of the protected alcohol. Preferred protecting groups for the alcohol moiety are silyl ethers such as a triethylsilyl or a tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosium tetrafluoroborate in a suitable anhydrous solvent such as dichloromethane, THF, DMF, or acetonitrile with or without an amine base such as pyridine or triethylamine affords the compound of the formula VA.

Scheme XIII

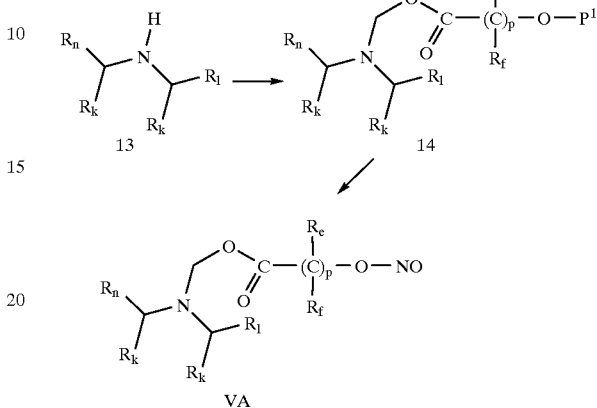

Nitroso compounds of formula (V) wherein $R_e$, $R_f$, $R_k$, $R_k$, $R_n$, and p are defined as above and an S-nitrosylated N-acyloxyalkyl amine is representative of the D group as defined above may be prepared according to Scheme XIV. The amine group of the compound of the formula 13 is converted to the N-acyloxyalkyl amine of the formula 15 wherein p, $R_e$, and $R_f$ are defined as above by reaction with an appropriate protected thiol containing chloromethyl acyl derivative wherein $P^2$ is as defined above. Preferred protecting groups for the thiol moiety are as a thioester such as a thioacetate or thiobenzoate, as a disulfide, as a thiocarbamate such as N-methoxymethyl thiocarbamate, or as a thioether such as a tetrahydropyranyl thioether. Deprotection of the thiol moiety (triphenylphosphine in water and sodium borohydride are preferred methods for reducing disulfide groups while aqueous base is typically utilized to hydrolyze thioesters and N-methoxymethyl thiocarbamates and mercuric trifluoroacetate or silver nitrate are used to remove a tetrahydropyranyl thioether group) followed by reaction a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methyene chloride, THF, DMF, or acetonitrile with or without an amine base such as pyridine or triethylamine affords the compound of the formula VB.

Scheme XIV

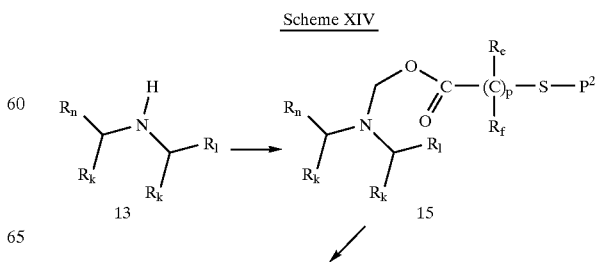

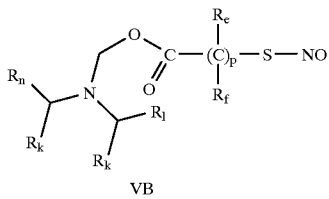

VB

Nitro compounds of formula (V) wherein $R_e$, $R_f$, $R_k$, $R_l$, $R_n$, and p are defined as above and an O-nitrosated N-acyloxyalkyl amine is representative of the D group as defined above may be prepared according to Scheme XV. The amine group of the compound of the formula 13 is converted to the N-acyloxyalkyl amine of the formula VC wherein p, $R_e$, and $R_f$ are defined as above by reaction with an appropriate nitrate containing chloromethyl acyl derivative. Preferred methods for the formation of N-acyloxyalkyl amines are reacting the amine with the preformed chloromethyl acyloxyalkyl derivative of the nitrate containing derivative to afford the compound of the formula VC.

Scheme XV

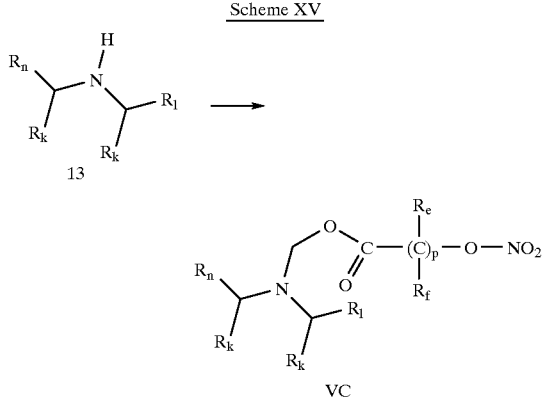

VC

Scheme XVI

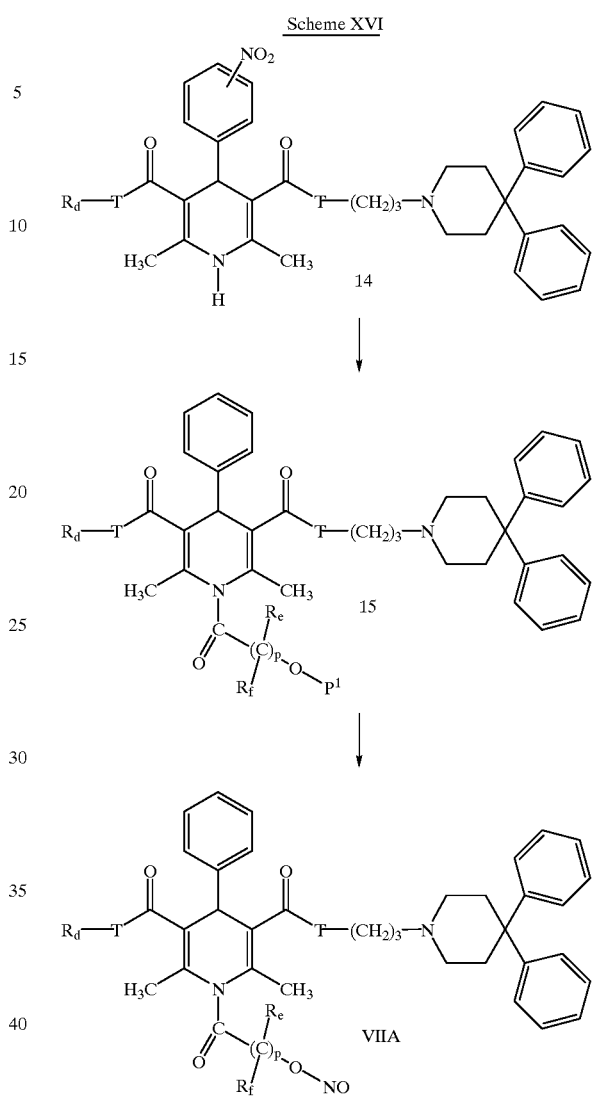

Nitroso compounds of formula (VII) wherein $R_d$, $R_e$, $R_f$, T, and p are defined as above and an O-nitrosylated amide is representative of the D group as defined above may be prepared according to Scheme XVI. The amine group of the dihydropyridine of the formula 14 is converted to the amide of the formula 15 wherein p, $R_e$ and $R_f$ are defined as above by reaction with an appropriate protected alcohol containing activated acylating agent wherein $P^1$ is as defined above. Preferred methods for the formation of amides are reacting the amine with the preformed acid chloride or symmetrical anhydride of the protected alcohol containing acid. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction a suitable nitrosylating agent such as thionyl chloride nitrite, thionyl dinitrite, or nitrosium tetrafluoroborate in a suitable anhydrous solvent such as dichloromethane, THF, DMF, or acetonitrile with or without an amine base such as pyridine or triethylamine affords the compound of the formula VIIA.

Nitroso compounds of formula (VII) wherein $R_d$, $R_e$, $R_f$, T, and p are defined as above and an S-nitrosylated amide is representative of the D group as defined above may be prepared according to Scheme XVII. The amine group of the dihydropyridine of the formula 14 is converted to the amide of the formula 16 wherein p, $R_e$ and $R_f$ are defined as above by reaction with an appropriate protected thiol containing activated acylating agent wherein $P^2$ is as defined above. Preferred methods for the formation of amides are reacting the amine with the preformed acid chloride or symmetrical anhydride of the protected thiol containing acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a S-triphenylmethyl thioether. Deprotection of the thiol moiety (zinc in dilute aqueous acid, triphenylphosphine in water and sodium borohydride are preferred methods for reducing disulfide groups while aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methyene chloride, THF, DMF, or acetonitrile with or without an amine base such as pyridine or triethylamine affords the compound of the formula VIIB. Alternatively, treatment of compound 16 with a stoichiometric quantity of sodium nitrite in aqueous acid affords the compound of the formula VIIB.

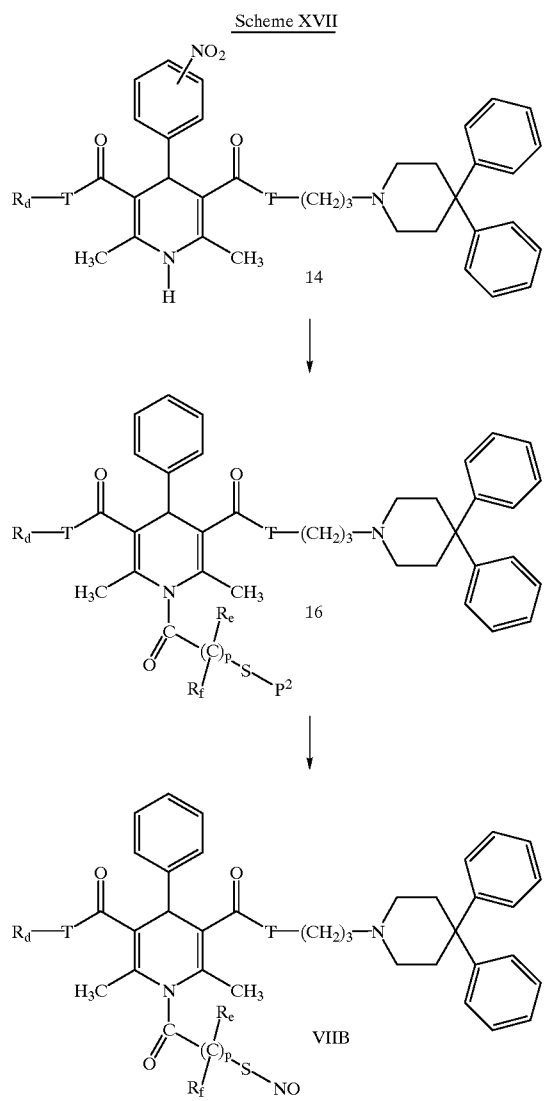

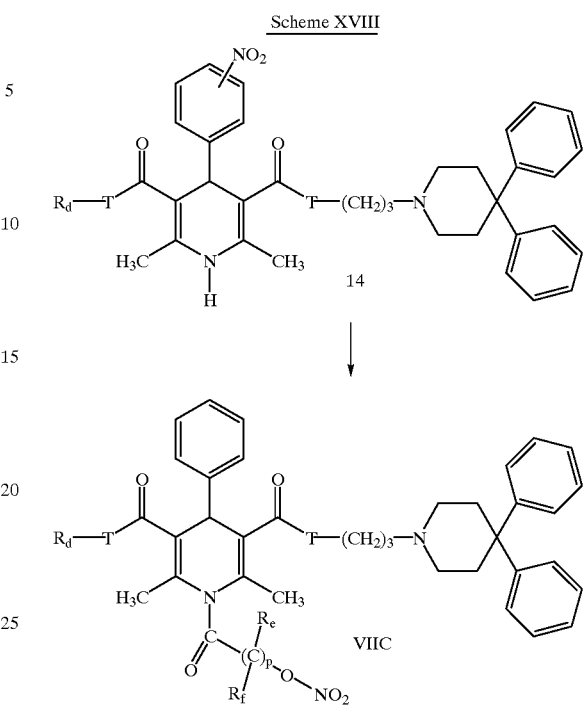

Nitro compounds of formula (VII) wherein $R_d$, $R_e$, $R_f$, T, and p are defined as above and an O-nitrosated amide is representative of the D group as defined above may be prepared according to Scheme XVIII. The amine group of the dihydropyridine of the formula 14 is converted to the amide of the formula VIIC wherein p, $R_e$ and $R_f$ are defined as above by reaction with an appropriate nitrate containing activated acylating agent. Preferred methods for the formation of amides are reacting the amine with the preformed acid chloride or symmetrical anhydride of the nitrate containing acid to afford the compound of the formula VIIC.

As noted above, another aspect the invention provides a composition comprising a therapeutically effective amount of an α-adrenergic receptor antagonist (α-antagonist), which can optionally be substituted with at least one NO or $NO_2$ moiety, and a compound that donates, transfers or releases nitric oxide as a charged species, i.e., nitrosonium ($NO^+$) or nitroxyl ($NO^-$), or as the neutral species, nitric oxide (NO●).

Another embodiment of this aspect is one where the α-blocker is not substituted with at least one NO or $NO_2$ moiety. Additional α-blockers that are suitable for this embodiment include amines, such as tedisamil, mirtazipine, setiptiline, reboxitine and delequamine; amides, such as indoramin and SB 216469; piperizines, such as SL 89.0591, ARC 239, urapidil, 5-methylurapidil and monatepil. Indoramin is a selective, competitive $α_1$-antagonist that has been used for the treatment of hypertension. Urapidil is also known to be a selective $α_1$-adrenergic antagonist that has a hypotensive effect in humans.

The compounds that donate, transfer or release nitric oxide can be any of those known to the art, including those mentioned and/or exemplified below.

Nitrogen monoxide can exist in three forms: $NO^-$ (nitroxyl), NO● (nitric oxide) and $NO^+$ (nitrosonium). NO● is a highly reactive short-lived species that is potentially toxic to cells. This is critical, because the pharmacological efficacy of NO depends upon the form in which it is delivered. In contrast to NO●, nitrosonium and nitroxyl do not react with $O_2$ or $O_2^-$ species, and are also resistant to decomposition in the presence of redox metals. Consequently, administration of NO equivalents does not result in the generation of toxic by-products or the elimination of the active NO moiety.

Compounds contemplated for use in the invention are nitric oxide and compounds that release nitric oxide or otherwise directly or indirectly deliver or transfer nitric oxide to a site of its activity, such as on a cell membrane, in vivo. As used here, the term "nitric oxide" encompasses uncharged nitric oxide (NO●) and charged nitric oxide species, particularly including nitrosonium ion (NO$^+$) and nitroxyl ion (NO$^-$). The reactive form of nitric oxide can be provided by gaseous nitric oxide. The nitric oxide releasing, delivering or transferring compounds, having the structure F—NO wherein F is a nitric oxide releasing, delivering or transferring moiety, include any and all such compounds which provide nitric oxide to its intended site of action in a form active for their intended purpose. As used here, the term "NO adducts" encompasses any of such nitric oxide releasing, delivering or transferring compounds, including, for example, S-nitrosothiols, S-nitrothiols, O-nitrosoalcohols, O-nitroalcohols, sydnonimines, 2-hydroxy-2-nitrosohydrazines (NONOates), (E)-alkyl-2-[(E)-hydroxyimino]-5-nitro-3-hexene amines or amides, nitrosoamines, as well a subtstates for the endogenous enzymes which synthesize nitric oxide. It is contemplated that any or all of these "NO adducts" can be mono- or poly-nitrosylated or nitrosated at a variety of naturally susceptible or artificially provided binding sites for nitric oxide or derivatives which donate or release NO.

One group of such NO adducts is the S-nitrosothiols, which are compounds that include at least one —S—NO group. Such compounds include S-nitroso-polypeptides (the term "polypeptide" includes proteins and also polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars, S-nitrosylated-modified and unmodified oligonucleotides (preferably of at least 5, and more particularly 5–200, nucleotides); and an S-nitrosylated hydrocarbons where the hydrocarbon can be a branched or unbranched, and saturated or unsaturated aliphatic hydrocarbon, or an aromatic hydrocarbon; S-nitrosylated hydrocarbons having one or more substituent groups in addition to the S-nitroso group; and heterocyclic compounds. S-nitrosothiols and the methods for preparing them are described in U.S. Pat. No. 5,380,758; Oae et al., Org. Prep. Proc. Int., 15(3):165–198 (1983); Loscalzo et al., J. Pharmacol. Exp. Ther., 249(3):726729 (1989) and Kowaluk et al., J. Pharmacol. Exp. Ther., 256:1256–1264 (1990), all of which are incorporated in their entirety by reference.

One particularly preferred embodiment of this aspect relates to S-nitroso amino acids where the nitroso group is linked to a sulfur group of a sulfur-containing amino acid or derivative thereof. For example, such compounds include the following: S-nitroso-N-acetylcysteine, S-nitroso-captopril, S-nitroso-homocysteine, S-nitroso-cysteine and S-nitroso-glutathione.

Suitable S-nitrosylated proteins include thiol-containing proteins (where the NO group is attached to one or more sulfur group on an amino acid or amino acid derivative thereof) from various functional classes including enzymes, such as tissue-type plasminogen activator (TPA) and cathepsin B; transport proteins, such as lipoproteins, heme proteins such as hemoglobin and serum albumin; and biologically protective proteins, such as the immunoglobulins and the cytokines. Such nitrosylated proteins are described in PCT Publ. Applic. No. WO 93/09806, published May 27, 1993. Examples include polynitrosylated albumin where multiple thiol or other nucleophilic centers in the protein are modified.

Further examples of suitable S-nitrosothiols include those having the structures:

(i) $CH_3[C(R_e)(R_f)]_xSNO$ wherein x equals 2 to 20 and $R_e$ and $R_f$ are as defined above;

(ii) $HS[C((R_e)(R_f)]_xSNO$ wherein x equals 2 to 20; and $R_e$ and $R_f$ are as defined above;

(iii) $ONS[C(R_e)(R_f)]_xB$; and (iv) $H_2N—(CO_2H)—(CH_2)_x—C(O)NH—C(CH_2SNO)—C(O)NH—CH_2—CO_2H$ wherein x equals 2 to 20; $R_e$ and $R_f$ are as defined above; and B is selected from the group consisting of fluoro, $C_1$–$C_6$ alkoxy, cyano, carboxamido, cycloalkyl, arylakoxy, alkylsulfinyl, arylthio, alkylamino, dialkylamino, hydroxy, carbamoyl, N-alkylcarbamoyl, N,N-dialkylcarbamoyl, amino, hydroxyl, carboxyl, hydrogen, nitro and aryl.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) to yield the S-nitroso derivative. Acids which may be used for this purpose include aqueous sulfuric, acetic and hydrochloric acids. Alternatively, the precursor thiol may be nitrosylated by treatment with an alkyl nitrite such as tert-butyl nitrite.

Another group of such NO adducts are those wherein the compounds donate, transfer or release nitric oxide and are selected from the group consisting of compounds that include at least one ON—N— or ON—C— group. The compound that includes at least one ON—N— or ON—C— group is preferably selected from the group consisting of ON—N— or ON—C—polypeptides (the term "polypeptide" includes proteins and also polyamino acids that do not possess an ascertained biological function, and derivatives thereof); ON—N— or ON—C—amino acids(including natural and synthetic amino acids and their stereoisomers and racemic mixtures); ON—N— or ON—C—sugars; ON—N— or ON—C—modified and unmodified oligonucleotides (preferably of at least 5, and more particularly 5–200, nucleotides), ON—O—, ON—N— or ON—C— hydrocarbons which can be branched or unbranched, saturated or unsaturated aliphatic hydrocarbons or aromatic hydrocarbons; ON—N— or ON—C— hydrocarbons having one or more substituent groups in addition to the ON—N— or ON—C— group; and ON—N— or ON—C— heterocyclic compounds.

Another group of such NO adducts is the nitrites which have an —O—NO group wherein the organic template to which the nitrite group is appended is a protein, polypeptide, amino acid, carbohydrate, branched or unbranched and saturated or unsaturated alkyl, aryl or a heterocyclic compound. A preferred example is the nitrosylated form of isosorbide. Compounds in this group form S-nitrosothiol intermediates in vivo in the recipient human or other animal to be treated and can therefore include any structurally analogous precursor R—O—NO of the S-nitrosothiols described above.

Another group of such adducts are nitrates which donate, transfer or release nitric oxide and are selected from the group consisting of compounds that include at least one at least one $O_2N$—O—, $O_2N$—N—, $O_2N$—S— or $O_2N$—C— group. Preferred among these are those selected from the group consisting of $O_2N$—O—, $O_2N$—N—, $O_2N$—S— or $O_2N$—C—polypeptides; $O_2N$—O—, $O_2N$—N—, $O_2N$—S— or $O_2N$—C—amino acids; $O_2N$—O—, $O_2N$—N—, $O_2N$—S— or $O_2N$—C—sugars; $O_2N$—O—, $O_2N$—N—, $O_2N$—S— or $O_2N$—C—modified and unmodified oligonucleotides; $O_2N$—O—, $O_2N$—N—, $O_2N$—S— or $O_2N$—C— hydrocarbons which can be branched or unbranched, saturated or unsaturated aliphatic hydrocarbons or aromatic hydrocarbons; $O_2N$—O—, $O_2N$—N—, $O_2N$—S— or $O_2N$—C— hydrocarbons having one or more substituent groups in addition to the O$_2$N—O—, O$_2$N—N—, O$_2$N—S— or O$_2$N—C—group; and O$_2$N—O—, O$_2$N—N—, O$_2$N—S— or O$_2$N—C—heterocyclic compounds. Preferred examples are isosorbide dinitrate and isosorbide mononitrate.

Another group of such NO adducts is the nitroso-metal compounds which have the structure $(R)_v$—A—M—(NO)$_v$. R includes polypeptides (the term "polypeptide" includes proteins and also polyamino acids that do not possess an ascertained biological function, and derivatives thereof); amino acids (including natural and synthetic amino acids and their stereoisomers and racemic mixtures and derivatives thereof); sugars; modified and unmodified oligonucleotides (preferably of at least 5, and more particularly 5–200, nucleotides); and a hydrocarbon where the hydrocarbon can be a branched or unbranched, and saturated or unsaturated aliphatic hydrocarbon, or an aromatic hydrocarbon; hydrocarbons having one or more substituent groups in addition to the Anitroso group; and heterocyclic compounds. A is S, O, or N, v is an integer independently selected from 1, 2 and 3, and M is a metal, preferably a transition metal. Preferred metals include iron, copper, manganese, cobalt, selenium and luthidium. Also contemplated are N-nitrosylated metal centers such as nitroprusside.

Another group of such adducts are N-oxo-N-nitrosoamines which donate, transfer or release nitric oxide and have a $R_1R_2$—N(O—M$^+$)—NO group wherein $R_1$ and $R_2$ include polypeptides, amino acids, sugars, modified and unmodified oligonucleotides, hydrocarbons where the hydrocarbon can be a branched or unbranched, and saturated or unsaturated aliphatic hydrocarbon or an aromatic hydrocarbon, hydrocarbons having one or more substituent groups and heterocyclic compounds. M$^+$ is a metal cation, such as, for example, a Group I metal cation.

Another group of such adducts are thionitrates which donate, transfer or release nitric oxide and have the structure $R_{10}$—S—NO$_2$ wherein $R_{10}$ includes polypeptides, amino acids, sugars, modified and unmodified oligonucleotides, and a hydrocarbon where the hydrocarbon can be a branched or unbranched, and saturated or unsaturated aliphatic hydrocarbon or an aromatic hydrocarbon.

Agents which stimulate endogenous NO synthesis such as L-arginine, the substrate for nitric oxide synthase, are also suitable for use in accordance with the invention.

When administered in vivo, the nitric oxide may be administered in combination with pharmaceutical carriers and in dosages described herein.

In another aspect the invention provides a method of treating male impotence in an individual in need thereof by administering to the individual a therapeutically effective amount of a composition comprising a nitrosated or nitrosylated α-antagonist of the invention in a pharmaceutically acceptable carrier.

In another aspect the invention provides a method of treating male impotence in an individual in need thereof which comprises treating an individual for male impotence by administering to the individual a therapeutically effective amount of a composition comprising an α-adrenergic receptor antagonist (α-antagonist), which can optionally be substituted with at least one NO or NO$_2$ moiety, and a compound that donates, transfers or releases nitric oxide in a pharmaceutically acceptable carrier.

Total daily dose administered to a host in single or divided doses may be in amounts, for example, from about 1 to about 100 mg/kg body weight daily and more usually about 3 to 30 mg/kg. Dosage unit compositions may contain such amounts of submultiples thereof to make up the daily dose.

The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

The compounds of the present invention may be administered orally, parenterally or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1, 3-butanediol. Among the acceptable vehicles and solvents that may be employed are water, Ringer's solution, and isotonic sodium chloride solution. In addition, sterile, fixed oils are conventionally employed an a solvent or suspending medium. For this purpose any bland fixed oil may be employed including synthetic mono- or diglycerides. in addition, fatty acids such as oleic acid find use in the preparation of injectables.

Solid dosage forms for oral administration may include capsules, tablets, pills, powders, granules and gels. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more compounds which are known to be effective against the specific disease state that one is targeting for treatment. The compositions of the invention can be administered as a mixture of an α-antagonist and a nitric oxide donor, they can also be used in combination with one or more compounds which are known to be effective against the specific disease state that one is targeting for treatment.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

EXAMPLE 1

N-(N-L-γ-glutamyl-S-Nitros-L-cysteinyl)glycine

N-(N-L-γ-glutamyl-L-cysteinyl)glycine (100 g, 0.325 mol) was dissolved in deoxygenated water (200 ml) and 2N HCl (162 ml) at room temperature and then the reaction mixture was cooled to 0° C. With rapid stirring, a solution of sodium nitrite (24.4 g, 0.35 mol) in water (40 ml) was added. Stirring with cooling of the reaction mixture was continued for approximately 1 hour after which time the pink precipitate which formed was collected by vacuum filtration. The filter cake was resuspended in chilled 40% acetone-water (600 ml) and collected by vacuum filtration. The filter cake was washed with acetone (2×200 ml) and ether (100 ml) and then dried under high vacuum at room temperature in the dark to afford the title compound as a pink powder. $^1$H NMR ($D_2O$)δ:1.98 (m, 2H), 2.32 (t, 2H), 3.67 (t, 1H), 3.82 (s 2H), 3.86 (dd, 1H), 3.98 (dd, 1H), 4.53 (m, 1H).

EXAMPLE 2

2-Acyl-17α(3-methyl-3-nitrosothiolbutoxy) yohimban-16α-carboxylic acid methyl ester hydrochloride salt 2a. 3-Methyl-3(2-tetrahydropyranyl)thiobutyric acid 3-Methyl-3-thiobutyric acid (4.2 g, 31 mmol), dihydropyran (2.8 ml, 31 mmol), and 200 μl of 4 N $HCl/Et_2O$ were allowed to stand at room temperature overnight. The volatiles were evaporated in vacuo (2 mm Hg) yielding 6.6 g (30 mmol) of material which was used without further purification. $^1$H-NMR ($CDCl_3$):δ 4.92 (d, J=8.1 Hz, 1H), 4.09 (d, J=10.5 Hz, 1H), 3.49–3.56 (mult, 1H), 2.73 (dd, J=1.2 and 13.7 Hz, Hz, 1H), 2.64 (d, J=13.8 Hz, 1H), 1.84–1.89 (mult 2H), 1.55–1.69 (mult, 4H), 1.51(s, 3H), 1.42 (s, 3H).

2b. 3,3'-Methyl-3,3'(2-tetrahydropyranyl)thiobutyric acid anhydride

The product of Example 2a (1.1 g, 5 mmol) and triethylamine (710 μl, 5 mmol) was dissolved in ethyl acetate (50 ml) and cooled to 0° C. Triphosgene (250 mg, 0.85 mmol) was added all in one portion and the reaction was stirred at 0° C. for 15 minutes then warmed to room temperature with continued stirring for 30 min. The precipitate which formed was removed by filtration and the filtrate was concentrated by rotary evaporation to afford 1.0 g (5 mmol) of the title compound. $^1$H-NMR ($CDCl_3$):δ 5.03–5.06 (mult, 2H), 4.04–4.08 (mult, 2H), 3.46–3.51 (mult, 2H), 2.89 (d, J=15.7 Hz, 2H), 2.77 (d, J=15.6 Hz, 2H), 1.79–1.88 (mult, 4H), 1.51–1.67 (mult, 8H), 1.54 (s, 6H), 1.49 (s, 6H).

2c. 17α (3-methyl-3-tetrahydropyranylthiolbutoxy) yohimban-16α-carboxylic acid methyl ester To a solution of yohimbine (1.6 g, 4.5 mmol) in pyridine (6 ml) was added the product of Example 2b (2.5 g, 6 mmol) and 4-dimethylaminopyridine (730 mg, 6 mmol). The reaction mixture was stirred at room temperature for 6 days. Acetonitrile (50 ml) was added to the reaction and then all of the volatile components were evaporated in vacuo. The residue was dissolved in ethyl acetate (100 ml) and washed with a 10% solution of aqueous sodium carbonate. The aqueous wash was then back extracted once with ethyl acetate. The combined organic extracts were washed with $H_2O$, brine, and then dried over anhydrous sodium sulfate. Treatment of the solution with activated charcoal followed by filtration and concentration of the filtrate in vacuo gave 2.8 g of a dark syrup.

Chromatography on silica gel eluting with 1:1 hexane/ethyl acetate containing 1% by volume triethylamine afforded 670 mg (20%) of the title compound. $^1$H-NMR ($CDCl_3$):δ 7.76 (s, 1H), 7.46 (d, J=7.2 Hz, 1H), 7.29 (dd, J=1.0 and 7.0 Hz, 1H), 7.12 (ddd; J=1.3, 7.1, and 7.1 Hz; 1H), 7.07 (ddd; J=1.1, 7.2, and 7.2 Hz; 1H), 5.46 (d, J=2.6 Hz, 1H), 5.07–5.11 (mult, 1H), 4.06–4.11 (mult, 1H), 3.69 (s, 3H), 3.47–3.55 (mult, 1H), 3.39 (d, J=10.4 Hz, 1H), 3.02–3.12 (mult, 2H), 2.97 (dd, J=4.5 and 12.2 Hz, 1H), 2.80 (d, J=14.3 Hz, 1H), 2.71 (mult, 1H), 2.69 (d, J=13.2 Hz, 1H), 2.61–2.65 (mult, 1H), 2.39 (dd, J=2.6 and 11.6 Hz, 1H), 2.23–2.33 (mult, 2H), 1.71–2.07 (mult, 5H), 1.58–1.69 (mult, 8H), 1.51 (s, 3H), 1.49 (s, 3H).

Anal Calcd for ($C_{31}H_{42}N_2O5S$-½ $H_2O$): C, 66.05; H, 7.69; N, 4.97; S, 5.69. Found C, 65.74; H, 7.33; N, 4.88; S, 5.57.

2d. 2-Acyl-17α(3-methyl-3-thiolbutoxy)yohimban-16α-carboxylic acid methyl ester

The product of Example 2c (620 mg, 1.1 mmol) was refluxed in a mixture of acetic acid (5 ml) and acetyl chloride (5 ml) for 4 hours. The solvent was evaporated in vacuo (2 mm Hg). The residue was partitioned between 5% aqueous ammonium hydroxide and ethyl acetate. The aqueous wash was extracted with ethyl acetate. The combined organic extracts were washed with brine and dried over anhydrous sodium sulfate. The solvent was evaporated in vacuo and the residue was chromatographed on silica gel eluting with 1:1 hexane/ethyl acetate containing 1% by volume triethylamine to afford 210 mg (34%) of 2-acyl-17u.(3-methyl-3-thioacetylbutoxy)yohimban-16 α-carboxylic acid methyl ester. This diacetate (180 mg, 0.32 mmol) was dissolved in acetic acid (4 ml) to which was added mercuric trifluoroacetate (190 mg, 0.45 mmol) and the reaction mixture was stirred at room temperature for 2 hours. The volatiles were evaporated in vacuo leaving a gum which was triturated with IN HCl (6 ml) to afford a yellow powder. The powder was partitioned between ethyl acetate and 10% aqueous ammonium hydroxide. The organic phase was filtered through Celite to remove the gray solid which was present and then the filtrate was washed with brine and then dried over anhydrous sodium sulfate.

Evaporation of the volatiles in vacuo afforded a solid which was chromatographed on silica gel eluting with a gradient of with 1:1 hexane/ethyl acetate containing 1% by volume triethylamine to ethyl acetate containing 1% by volume triethylamine to yield 60 mg (37%) of the title compound as a white powder. $^1$H-NMR ($CDCl_3$):δ 7.81 (d, J=7.0 Hz, 1H), 7.41 (d, J=6.8 Hz, 1H), 7.23–7.29 (mult, 2H), 5.46 (s, 1H), 4.17 (d, J=9.9 Hz, 1H), 3.64 (s, 3H), 3.11–3.15 (mult, 1H), 3.00 (dd, J=3.5 and 12.4 Hz, 1H), 2.64–2.84 (mult, 10H), 2.31 (dd, J=2.6 and 11.7 Hz, 1H), 2.24 (d, J=12.7 Hz, 1H), 2.04–2.08 (mult, 2H), 1.41–1.62 (mult, 11H). $^{13}$C-NMR ($CDCl_3$):δ 171.6, 170.7, 169.5, 13 7.3, 136.4, 129.6, 124.1, 122.9, 118.3, 117.2, 114.6, 70.0, 61.0, 59.8, 51.9, 51.8, 50.9, 47.7, 45.6, 37.8, 37.6, 36.22, 36.2, 33.2, 29.9, 27.1, 23.8, 22.3.

2e. 2-Acyl-17α(3-methyl-3-nitrosothiolbutoxy)yohimban-16α-carboxylic acid methyl ester hydrochloride salt To a slurry of the compound of Example 2d (40 mg, 0.078 mmol) in 1:1 methanol/IN HCI (4 ML) with dimethylformamide (400 μl) was added a solution of sodium nitrite (11 mg, 0.16 mmol) in $H_2O$ (200 μl). The white powder turned green as the slurry was stirred at room temperature for 25 minutes. At this juncture dimethylformamide (600 μl) and additional aqueous sodium nitrite (11 mg in 200 μl of H₂O) was added and stirring at room temperature was continued for an additional 15 minutes. The reaction mixture was partitioned between CHCl₃ and H₂O adding 10% aqueous ammonium hydroxide to the aqueous phase until basic to pH paper. The aqueous layer was extracted with CHCl₃ and the combined organic extracts were washed with brine and then dried over anhydrous sodium sulfate. The volatiles were evaporated in vacuo and the residue was dissolved in ether. The product was precipitated with ethereal HCl to afford 19 mg of the title compound as a green solid. $^1$H-NMR (CDCl₃) :δ 7.81 (dd, J=1.7 and 6.8 Hz, 1H), 7.42 (d, J=6.8 Hz, 1H), 7.23–7.29 (mult, 2H), 5.43 (d, J=2.6 Hz, 1 H), 4.15 (d, J=9.8 Hz, 1H), 3.63 (s, 3H), 3.36 (d, J=15.1 Hz, 1H), 3.30 (d, J=15.1 Hz, 1H), 3.12 (dd, J=4.9 and 11.0 Hz, 1H), 3.00 (dd, J=3.7 and 12.3 Hz, 1H), 2.72 (s, 3H), 2.63–2.82 (mult, 3H), 2.31 (dd, J=2.6 and 11.7 Hz, 1H), 2.03 (s, 3H), 2.00 (s, 3H), 1.0–2.0 (mult, 9H).

EXAMPLE 3

In Vivo Comparative Erectile Responses

Male New Zealand white rabbits weighing 2.5 kg were used as the animal model. Animals were first relaxed with an i.m. injection of 25 mg/kg ketamine prior to anesthesia with a bolus i.v. injection of 10 mg/kg Profol and maintained with i.v. infusion at 0.5 mg/kg/min. Ventilation of the animals was performed with 1% halothane plus 0.8 L/min O₂ and 1 L/min N₂O. A 22 gauge angiocatheter was placed in the femoral artery for measurement of systemic blood pressure. A dorsal incision was made in the penis and the corpora cavernosa exposed and cannulated with a 21 gauge butterfly needle to measure intracavernosal pressure.

Drugs at various concentrations were delivered intracavernosally at a volume of 150 μl through a 25 gauge needle. A 150 μl solution of a mixture of papaverine (30 mg/kg), phentolamine (1 mg/kg) and prostaglandin E1 (10 μg/ml) (pap/phent/PGE1) was injected in the corpora as a standard solution for comparison with the response of yohimbine, Example 1, Example 2, and the combination of yohimbine and Example 1. This pap/phent/PGE1 mixture is considered to cause a maximal erection-inducing effect.

Figure 2:
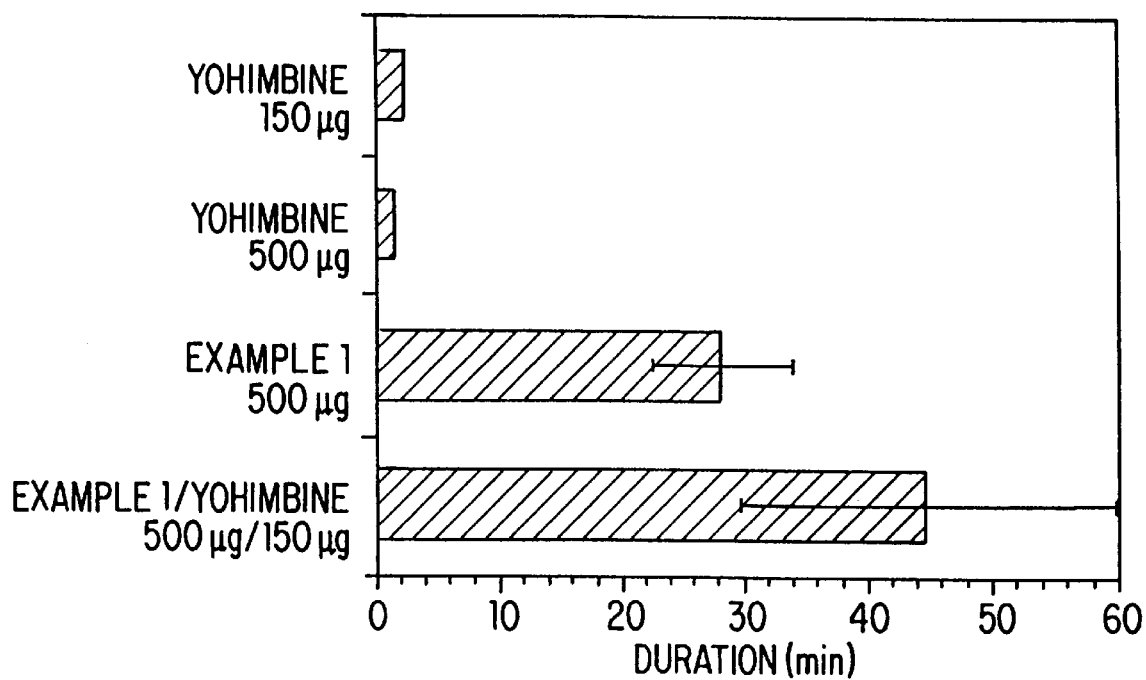
FIG. 2 shows the duration of the erectile response in vivo in the anesthetized rabbit upon intracavemosal administration of yohimbine (150 μg, 500 μg), Example 1 (500 μg), and a combination of yohimbine (150 μg) and Example 1 (500 μg). The ordinate indicates the various drugs given and the abscissa is the duration in minutes.

As shown in FIG. 1, yohimbine dose dependently induced erectile response in the anesthetized rabbit. A 500 μg dose of Example 1 was able to induce near maximal response relative to the standard dose of pap/phent/PGE1. A combination of the submaximal dose of yohimbine (150μg) and Example 1 (500 μg) also induced maximum erectile response. Yohimbine at both the submaximal and maximal efficacy doses produced very short duration of action (FIG. 2). Example 1 produced a much longer duration of action. The duration of action is potentiated by a combination of Example 1 and yohimbine which is longer than the sum of the duration of each of these compounds alone (FIG. 2).

Figure 3:
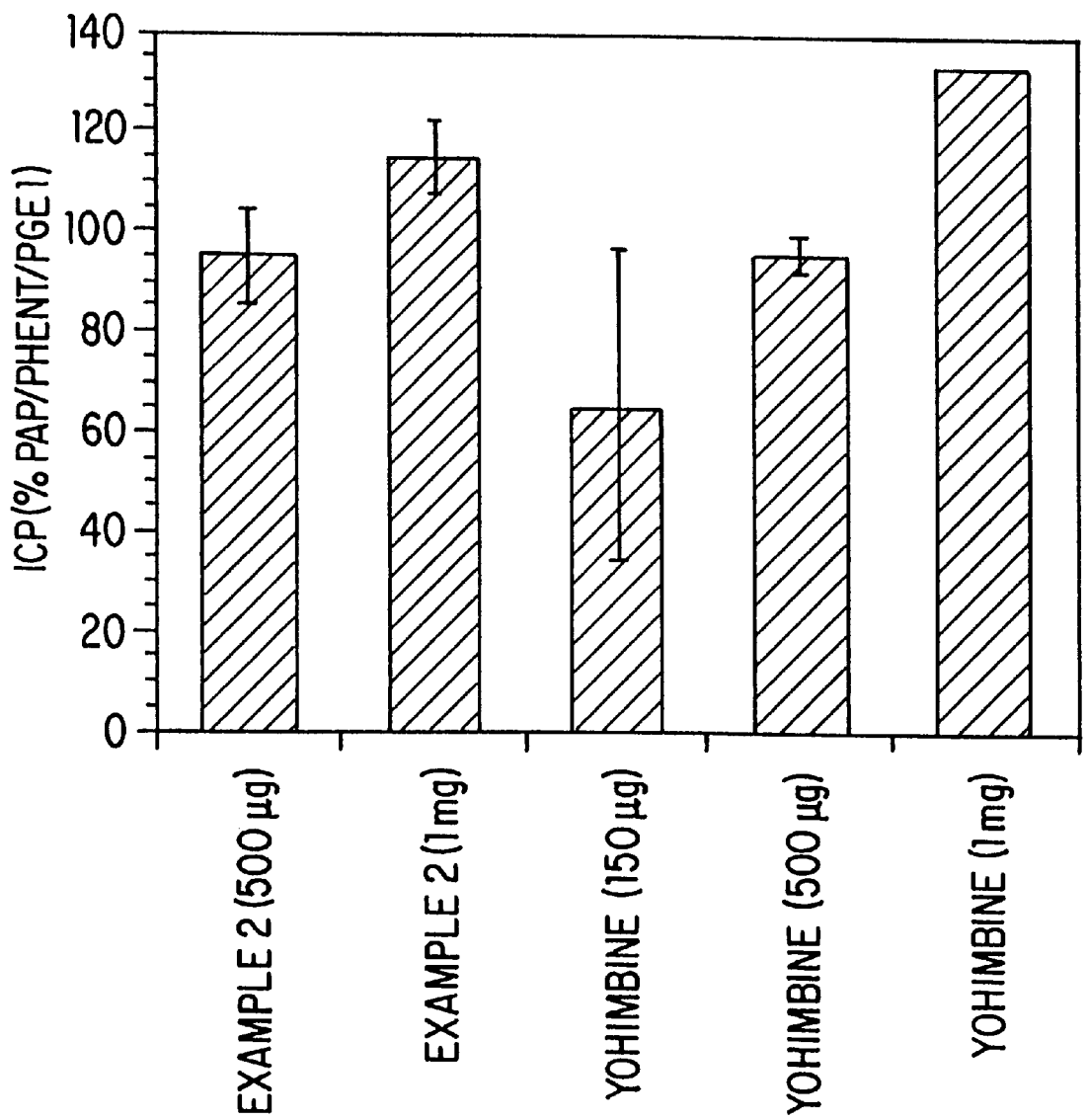
FIG. 3 shows the percent peak erectile response in vivo compared to that produced by 150 μl of pap/phent/PGE1 (30 mg/ml: 1 mg/ml: 10 μg/ml) in the anesthetized rabbit following the intracavemosal injection of 150 μl of yohimbine (150 μg, 500 μg and 1 mg) and Example 2 (500 μg, 1 mg). The ordinate is the percent response of intracavernosal pressure relative to that produced by pap/phent/PGE1 and the abscissa indicates the various doses of yohimbine and Example 2 given.
Figure 4:
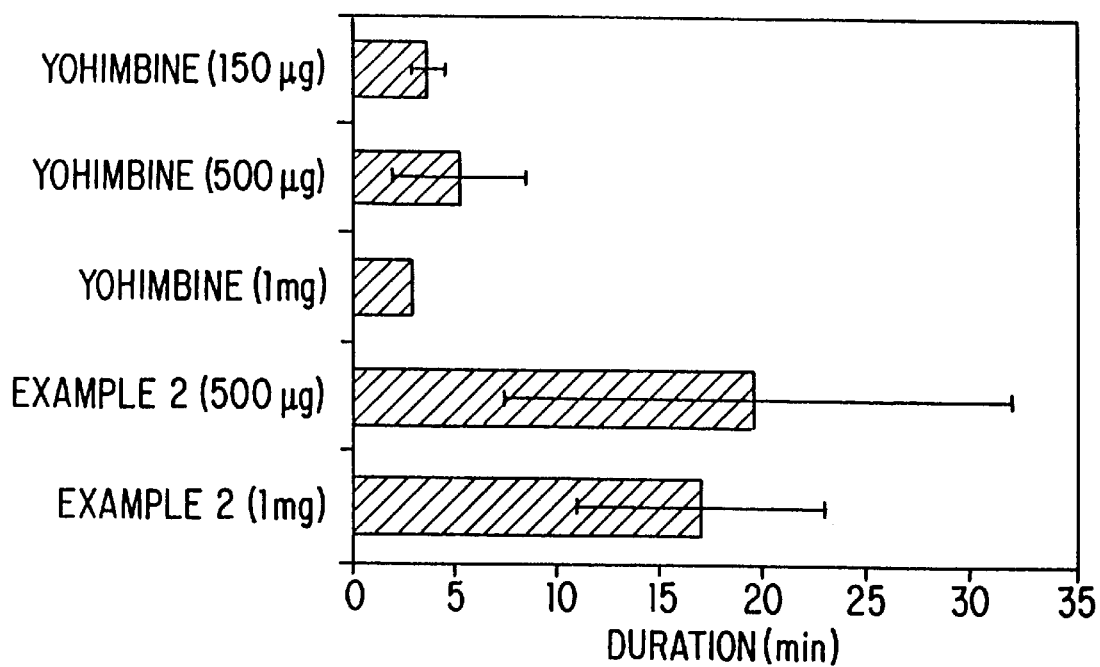
FIG. 4 shows the duration of the erectile response in vivo in the anesthetized rabbit upon intracavernosal administration of yohimbine (150 μg, 500 μg and 1 mg) and Example 2 (500 μg and 1 mg). The ordinate indicates the various doses of yohimbine and Example 2 given and the abscissa is the duration in minutes.

FIG. 3 shows that Example 2 at the 500 μg dose is equipotent to the standard dose of pap/phent/PGE 1. A higher dose of Example 2 (1 mg) is at least equal to or more efficacious that the standard dose of the pap/phent/PGE1 mixture. FIG. 4 shows that Example 2 has the advantage of producing longer duration of action compared to yohimbine. FIG. 5 demonstrates that a dose (500 μg) of Example 2 effective in the erectile response did not produce any effect on systemic blood pressure upon intracavernosal injection. However, a standard dose of the mixture of pap/phent/PGE1 produced a significant decrease in systemic blood pressure upon intracavernosal injection, suggesting that Example 2 lacks this side effect.

FIG. 1 shows the percent peak erectile response in vivo compared to that produced by 150 μl of pap/phent/PGE1 (30 mg/ml: 1 mg/ml: 10 μg/ml) in the anesthetized rabbit following the intracavernosal injection of 150 μl of yohimbine (150 μg, 500 μg), Example 1 (500 μg), and a combination of yohimbine (150 μg) and Example 1 (500 μg). The ordinate is the percent response of intracavernosal pressure relative to that produced by pap/phent/PGE1 and the abscissa indicates the various drugs given.

FIG. 2 shows the duration of the erectile response in vivo in the anesthetized rabbit upon intracavernosal administration of yohimbine (150 μg, 500 μg), Example 1 (500 μg), and a combination of yohimbine (150 μg) and Example 1 (500 μg). The ordinate indicates the various drugs given and the abscissa is the duration in minutes.

FIG. 3 shows the percent peak erectile response in vivo compared to that produced by 150 til of pap/phent/PGE1 (30 mg/ml: 1 mg/ml: 10 μg/ml) in the anesthetized rabbit following the intracavemosal injection of 150 gl of yohimbine (150 μg, 500 μg and 1 mg) and Example 2 (500 μg, 1 mg). The ordinate is the percent response of intracavernosal pressure relative to that produced by pap/phent/PGE1 and the abscissa indicates the various doses of yohimbine and Example 2 given.

FIG. 4 shows the duration of the erectile response in vivo in the anesthetized rabbit upon intracavernosal administration of yohimbine (150 μg, 500 μg and 1 mg) and Example 2 (500 μg and 1 mg). The ordinate indicates the various doses of yohimbine and Example 2 given and the abscissa is the duration in minutes.

Figure 5A:
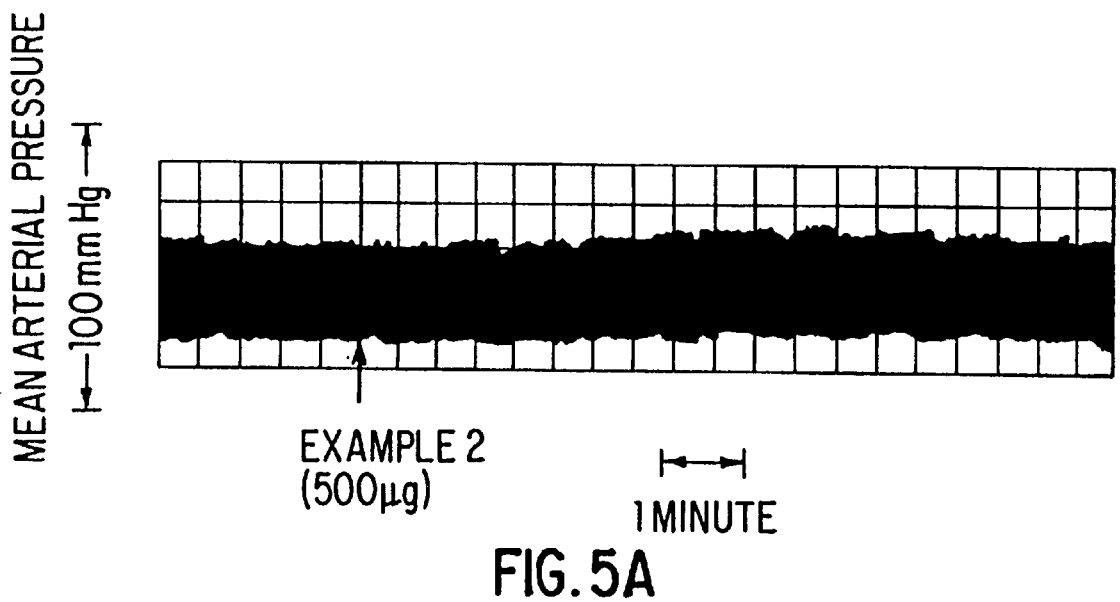
FIG. 5A shows the effects of intracavernosal injections of Example 2 (500 μg) on systemic blood pressure in the anesthetized rabbit.
Figure 5B:
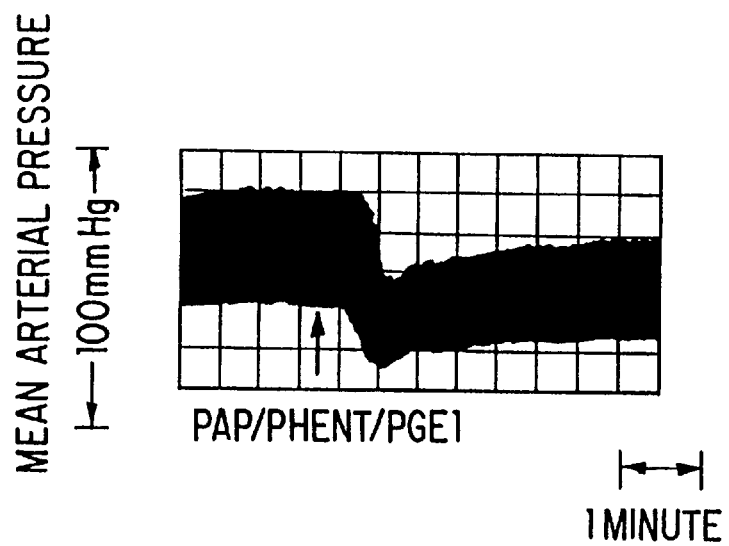
FIG. 5B shows the effects of intracavernosal injections of the standard mixture of pap/phent/PGE1 on systemic blood pressure in the anesthetized rabbit.

FIGS. 5A and 5B compare the effects of intracavernosal injections of Example 2 (500 μg) and the standard mixture of pap/phent/PGE1 on systemic blood pressure in the anesthetized rabbit.

What is claimed is:

1. A nitrosated or nitrosylated α-adrenergic receptor antagonist which is a compound having the structure:

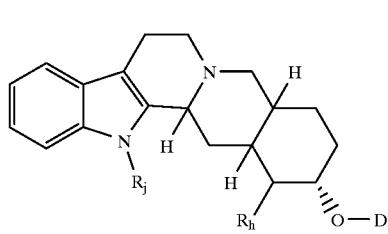

III wherein $R_h$ is hydrogen, —C(O)—OR$_d$ or —C(O)—X wherein X is (1) —Y—(C(R$_e$)(R$_f$))$_p$—G—(C(R$_e$)(R$_f$))$_p$—T—Q; wherein G is (i) a covalent bond; (ii) —T—C(O)—; (iii) —C(O)—T—; or (iv) —C(Y—C(O)—R$_m$)— wherein R$_m$ is a mono- or bi-cyclic ring system containing one or two aromatic rings and comprising at least one nitrogen, oxygen or sulfur atom in at least one aromatic ring, and that is unsubstituted or substituted with one, two or three substituents independently selected from lower alkyl, haloalky, alkoxy, amino, alkylamino, dialkylamino, hydroxy, halo and nitro, or R$_m$ is a 3-, 4-, 5-, 6-, or 7-membered non-aromatic ring containing at least one nitrogen atom, oxygen, or sulfur atom; Y is oxygen, sulfur, or NR$_i$ in which R$_i$ is hydrogen or lower alkyl; R$_d$ is hydrogen, lower alkyl, or cycloalkyl, or R$_d$ is a mono- or bi-cyclic carbocyclic ring system having one or two aromatic rings which is unsubstituted or substituted with one, two or three substituents independently selected from lower alkyl, haloalkyl, alkoxy, amino, alkylamino, dialkylamino, hydroxy, halo, and nitro, or $R_d$ is a mono- or bi-cyclic ring system containing one or two aromatic rings and comprising at least one nitrogen, oxygen or sulfur atom in at least one aromatic ring, and is unsubstituted or substituted with one, two or three substituents independently selected from lower alkyl, haloalkyl, alkoxy, amino, alkylamino, dialkylamino, hydroxy, halo and nitro; $R_e$ and $R_f$ are independently selected from hydrogen, lower alkyl, cycloalkyl, alkylamino and dialkylamino, or $R_e$ and $R_f$ are independently selected from a mono- or bi-cyclic carbocyclic ring system having one or two aromatic rings which is unsubstituted or substituted with one, two or three substituents independently selected from lower alkyl, haloalkyl, alkoxy, amino, alkylamino, dialkylamino, hydroxy, halo, and nitro, or $R_e$ and $R_f$ are independently selected from a mono- or bi-cyclic ring system containing one or two aromatic rings and comprising at least one nitrogen, oxygen or sulfur atom in at least one aromatic ring, and that is unsubstituted or substituted with one, two or three substituents independently selected from lower alkyl, haloalkyl, alkoxy, amino, alkylamino, dialkylamino, hydroxy, halo and nitro, or $R_e$ and $R_f$ are independently a lower alkyl appended to a mono- or bi-cyclic ring system having one or two aromatic rings that is unsubstituted or substituted with one, two or three substituents indpendently selected from lower alkyl, halo alkyl, alkoxy, amino, alkylamino, dialkylamino, hydroxy, halo and nitro, or $R_e$ and $R_f$ taken together are carbonyl, cycloalkyl or bridged cycloalkyl, p is an integer from 1 to 6 and T is a covalent bond, oxygen, sulfur or nitrogen and Q is —NO or —NO$_2$; or (2)

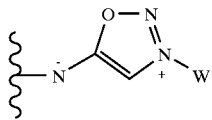

wherein W is a 3-, 4-, 5-, 6-, or 7-membered non-aromatic ring containing at least one nitrogen atom, oxygen, or sulfur atom, or W is $NR_iR'_i$ wherein $R_i$ and $R'_i$ are independently selected from lower alkyl and alkenyl, or $R_i$ or $R'_i$ are independently selected from a mono- or bi-cyclic carbocyclic ring system having one or two aromatic rings which may be unsubstituted or substituted with one, two or three substituents independently selected from lower alkyl, haloalkyl, alkoxy, amino, alkylamino, dialkylamino, hydroxy, halo, and nitro; and wherein $R_j$ is —D or —(O) $CR_d$, and D is (i) —NO, (ii) —NO$_2$; (iii) —C($R_d$)—O—C (O)—Y—(C($R_e$)($R_f$))$_p$—T—Q in which $R_d$, Y, $R_e$, $R_f$, p, T and Q are as defined above; (iv) —(CO)—T$^1$—(C($R_e$)($R_f$))$_p$—T$^2$—Q wherein T$^1$ and T$^2$ are independently selected from T, and $R_e$, $R_f$, p and T are defined above; or (v) —C(O)—T(C($R_y$)($R_z$))$_p$ wherein $R_y$ and $R_z$ are independently selected from —T$^1$—(C($R_e$)($R_f$))$_p$—G—(C($R_e$)($R_f$))$_p$—T$^2$—Q wherein G, $R_d$, $R_e$, $R_f$, p Q and T are as defined above.

2. The compound of claim 1 wherein the α-adrenergic receptor antagonist is a compound which has been nitrosated or nitrosylated through a site selected from the group consisting of oxygen, sulfur, carbon and nitrogen.

3. A compound according to claim 1, wherein
(a) the mono- or bicyclic ring system having one or two aromatic rings is a member selected from the group consisting of phenyl, naphthyl, tetrahydronaphthyl, indanyl, indenyl, each group of which can be unsubstituted or substituted with one, two or three substituents independently selected from loweralkyl, haloalkyl, alkoxy, amino, alkylamino, dialkylamino, hydroxy, halo, and nitro or may be tetrafluorophenyl and pentafluorophenyl; and (b) the mono- or bi-cyclic ring system containing one or two aromatic rings and comprising at least one nitrogen, oxygen or sulfur atom in at least one aromatic ring is a member selected from the group consisting of pyridine, pyrazine, pyrimidine, pyridazine, pyrazole, triazole, thiazole, isothiazole, benzothiazole, benzoxazole, thiadiazole, oxazole, pyrrole, imidazole and isoxazole, each group of which can be unsubstituted or substituted with one, two or three substituents independently selected from lower alkyl, haloalkyl, alkoxy, amino, alkylamino, dialkylamino, hydroxy, halo and nitro.

4. A compound according to claim 1, wherein said compound is a member selected from the group consisting of 2-acyl-17α(3-methyl-3-nitrosothiolbutoxy) yohimban-16α-carboxylic acid $C_1$–$C_4$ alkyl ester and acid addition salts thereof.

5. A composition comprising the nitrosated or nitrosylated α-adrenergic receptor antagonist of claim 1 and a pharmaceutically acceptable carrier.

6. A method of treating male impotence in an individual in need thereof which comprises treating an individual for male impotence by administering to the individual a therapeutically effective amount of at least one compound according to claim 1 in a pharmaceutically acceptable carrier.

7. A composition comprising (i) a therapeutically effective amount of at least one nitrosated or nitrosylated α-adrenergic receptor antagonist compound according to claim 1 and (ii) a S-nitrosothiol compound, wherein the S-nitrosothiol compound donates, transfers or releases nitric oxide or elevates endogenous synthesis levels of nitric oxide.

8. The composition of claim 7 wherein the nitrosated or nitrosylated α-adrenergic receptor antagonist compound is a nitrosated or nitrosylated member selected from the group consisting of yohimbine β-yohimbine, yohimbol, pseudoyohimbine and epi-3α-yohimbine.

9. The composition according to claim 7 wherein said S-nitrosothiol compound is S-nitroso-N-acetylcysteine S-nitroso-captopril, S-nitroso-homocysteine, S-nitroso-cysteine, or S-nitroso-glutathione.

10. The composition of claim 7 wherein the S-nitrosothiol is:

(i) $CH_3(C(R_e)(R_f))_xSNO$;
(ii) $HS(C(R_e)(R_f))_xSNO$;
(iii) $ONS(C(R_e)(R_f))_xB$; or
(iv) $H_2N—(CO_2H)—(CH_s)_x—C(O)NH—C(CH_2SNO)—C(O)NH—CH_2—CO_2H$ wherein x equals 2 to 20; $R_e$ and $R_f$ are independently selected from hydrogen, lower alkyl, cycloalkyl, alkylamino and dialkylamino, or $R_e$ and $R_f$ are independently selected from a mono- or bi-cyclic carbocyclic ring system having one or two aromatic rings which is unsubstituted or substituted with one, two or three substituents independently selected from lower alkyl, haloalkyl, alkoxy, amino, alkylamino, dialkylamino, hydroxy, halo, and nitro, or $R_e$ and $R_f$ are independently selected from a mono- or bi-cyclic ring system containing one or two aromatic rings and comprising at least one nitrogen, oxygen or sulfur atom in at least one aromatic ring, and that is unsubstituted or substituted with one, two or three substituents independently selected from lower alkyl, haloalkyl, alkoxy, amino, alkylamino, dialkylamino, hydroxy, halo and nitro, or $R_e$ and $R_f$ are independently a lower alkyl appended to a mono- or bi-cyclic ring system having one or two aromatic rings that is unsubstituted or substituted with one, two or three substituents indpendently selected from lower alkyl, halo alkyl, alkoxy, amino, alkylamino, dialkylamino, hydroxy, halo and nitro, or $R_e$ and $R_f$ taken together are carbonyl, cycloalkyl or bridged cycloalkyl; and B is selected from the group consisting of fluoro, alkoxy, cyano, carboxamido, cycloalkyl, arylkoxy wherein the aryl group is a mono- or bi-cyclic carbocyclic ring system having one or two aromatic rings, alkylsulfinyl, arylthio wherein the aryl group is a mono- or bi-cyclic carbocyclic ring system having one or two aromatic rings, alkylamino, dialkylamino, hydroxy, carbamoyl, N-alkylcarbamoyl, N,N-dialkylcarbamoyl, amino, hydroxyl, carboxyl, hydrogen, nitro and a mono- or bi-cyclic carbocyclic ring system having one or two aromatic rings.

11. A method of treating male impotence in an individual in need thereof which comprises treating an individual for male impotence by administering to the individual a therapeutically effective amount of a composition according to claim 7 in a pharmaceutically acceptable carrier.

12. A composition comprising (i) a therapeutically effective amount of at least one nitrosated or nitrosylated α-adrenergic receptor antagonist compound according to claim 1 and (ii) a compound that donates, transfers or releases nitric oxide or elevates endogenous synthesis levels of nitric oxide, wherein the compound that donates, transfers or releases nitric oxide or elevates endogenous synthesis levels of nitric oxide is selected from the group consisting of:

(i) compounds that include at least one ON—O—, ON—N— or ON—C— group;

(ii) a N-oxo-N-nitrosoamine which has an $R_1R_2$—N(O—$M^+$)—NO group, wherein $M^+$ is a metal cation, and $R_1$ and $R_2$ independently include polypeptides, amino acids, sugars, oligonucleotides, a branched or unbranched, saturated or unsaturated aliphatic hydrocarbon, a mono- or bicyclic carbocyclic ring system having one or two aromatic rings, hydrocarbons having one or more substituent groups, a heterocyclic compound which is a mono- or bi-cyclic ring system containing one or two aromatic rings and comprising at least one nitrogen, oxygen or sulfur atom in at least one aromatic ring, or a heterocyclic compound which is a 3-, 4-, 5-, 6-, or 7-membered non-aromatic ring containing at least one nitrogen atom, oxygen, or sulfur atom;

(iii) a thionitrate which has the structure $R_{10}$—S—$NO_2$ wherein $R_{10}$ includes polypeptides, amino acids, sugars, oligonucleotides, a branched or unbranched, saturated or unsaturated aliphatic hydrocarbon or a mono- or bicyclic carbocyclic ring system having one or two aromatic rings; and (iv) a nitrate which has the structure $R_{10}$—O—$NO_2$ wherein $R_{10}$ is as defined above.

13. The composition of claim 12 wherein the nitrosated or nitrosylated α-adrenergic receptor antagonist is a nitrosated or nitrosylated member selected from the group consisting of yohimbine, β-yohimbine, yohimbol, pseudoyohimbine and epi-3α-yohimbine.

14. The composition of claim 12, wherein the compounds that include at least one ON—O—, ON—N— or ON—C— group are selected from the group consisting of a ON—N—polypeptide, an ON—C—polypeptide, an ON—N—amino acid, an ON—C—amino acid, an ON—13 sugar, an ON—C—sugar, an ON—N—oligonucleotide, an ON—C—oligonucleotide, a straight or branched, saturated or unsaturated, substituted or unsubstituted, aliphatic or aromatic ON—N—hydrocarbon, a straight or branched, saturated or unsaturated, substituted or unsubstituted, aliphatic or aromatic ON—C—hydrocarbon, a straight or branched, saturated or unsaturated, aliphatic or aromatic ON—O—hydrocarbon, a ON—N—heterocyclic compound which is a mono- or bi-cyclic ring system containing one or two aromatic rings and comprising at least one nitrogen, oxygen or sulfur atom in at least one aromatic ring or a heterocyclic compound which is a 3-, 4-, 5-, 6-, or 7-membered non-aromatic ring containing at least one nitrogen atom, oxygen, or sulfur atom, and a ON—C—heterocyclic compound which is a mono- or bi-cyclic ring system containing one or two aromatic rings and comprising at least one nitrogen, oxygen or sulfur atom in at least one aromatic ring or a heterocyclic compound which is a 3-, 4-, 5-, 6-, or 7-membered non-aromatic ring containing at least one nitrogen atom, oxygen, or sulfur atom.

15. A method of treating male impotence in an individual in need thereof comprising treating the individual for male impotence by administering to the individual a therapeutically effective amount of at least one compound according to claim 12 in a pharmaceutically acceptable carrier.

16. A composition comprising (i) the nitrosated or nitrosylated α-adrenergic receptor antagonist of claim 1 and (ii) L-arginine.

17. A method of treating male impotence in an individual in need thereof comprising treating the individual for male impotence by administering to the individual a therapeutically effective amount of at least one composition according to claim 16 in a pharmaceutically acceptable carrier.

18. A composition comprising (i) the nitrosated or nitrosylated α-adrenergic receptor antagonist of claim 1 and (ii) a compound that donates, transfers or releases nitric oxide or elevates endogenous synthesis levels of nitric oxide, wherein the compound that donates, transfers or releases nitric oxide or elevates endogenous synthesis levels of nitric oxide is a compound comprising at least one $O_2N$—O—, $O_2N$—N—, $O_2N$—S— or $O_2N$—C— group.

19. The composition of claim 18, wherein the compound comprising at least one $O_2N$—O—, $O_2N$—N—, $O_2N$—S— or $O_2N$—C— group is an $O_2N$—O—polypeptide, an $O_2N$—N—polypeptide, an $O_2N$—S—polypeptide, an $O_2N$—C—polypeptide, an $O_2N$—O—amino acid, an $O_2N$—N—amino acid, an $O_2N$—S—amino acid, an $O_2N$—C—amino acid, an $O_2N$—O—sugar, an $O_2N$—N—sugar, an $O_2N$—S—sugar, an $O_2N$—C—sugar, an $O_2N$—O—oligonucleotide, an $O_2N$—N—oligonucleotide, an $O_2N$—S—oligonucleotide, an $O_2N$—C—oligonucleotide, a straight or branched, saturated or unsaturated, substituted or unsubstituted, aliphatic or aromatic $O_2N$—O—hydrocarbon, a straight or branched, saturated or unsaturated, substituted or unsubstituted, aliphatic or aromatic $O_2N$—N—hydrocarbon, a straight or branched, saturated or unsaturated, substituted or unsubstituted, aliphatic or aromatic $O_2N$—S—hydrocarbon, a straight or branched, saturated or unsaturated, substituted or unsubstituted, aliphatic or aromatic $O_2N$—C—hydrocarbon, an $O_2N$—O—heterocyclic compound which is a mono- or bi-cyclic ring system containing one or two aromatic rings and comprising at least one nitrogen, oxygen or sulfur atom in at least one aromatic ring or a compound which is a 3-, 4-, 5-, 6-, or 7-membered non-aromatic ring containing at least one nitrogen atom, oxygen, or sulfur atom, an $O_2N$—N—heterocyclic compound which is a mono- or bi-cyclic ring system containing one or two aromatic rings and comprising at least one nitrogen, oxygen or sulfur atom in at least one aromatic ring or a compound which is a 3-, 4-, 5-, 6-, or 7-membered non-aromatic ring containing at least one nitrogen atom, oxygen, or sulfur atom, an $O_2N$—S—heterocyclic compound which is a mono- or bi-cyclic ring system containing one or two aromatic rings and comprising at least one nitrogen, oxygen or sulfur atom in at least one aromatic ring or a compound which is a 3-, 4-, 5-, 6-, or 7-membered non-aromatic ring containing at least one nitrogen atom, oxygen, or sulfur atom or an $O_2N$—C—heterocyclic compound which is a mono- or bi-cyclic ring system containing one or two aromatic rings and comprising at least one nitrogen, oxygen or sulfur atom in at least one aromatic ring or a compound which is a 3-, 4-, 5-, 6-, or 7-membered non-aromatic ring containing at least one nitrogen atom, oxygen, or sulfur atom.

20. A method of treating male impotence in an individual in need thereof comprising treating the individual for male impotence by administering to the individual a therapeutically effective amount of at least one composition according to claim 18 in a pharmaceutically acceptable carrier.

* * * * *

UNITED STATES PATENT AND TRADEMARK OFFICE
CERTIFICATE OF CORRECTION

PATENT NO.     : 5,932,538
DATED          : August 3, 1999
INVENTOR(S)    : Garvey et al It is certified that error appears in the above-identified patent and that said Letters Patent is hereby corrected as shown below:

Column 2:
Line 4, after "carrier." delete "pharma-"
Line 5, delete "ceutically acceptable carrier."
Line 48, change "intracavemosal" to --intracavenosal--.
Line 56, change "intracavemosal" to --intracavenosal--.

Column 3:
Line 37, change "$R_2$" to --$R_{12}$--.

Column 5:
Line 27, change "cyohimbine" to --yohimbine--.

Column 23:
Line 19, change "4-dimethylaminopyridine" to -- 4-dimethylamino-pyridine --.

Column 30:
Line 55, delete the second occurrence of "at".
Line 56, delete "least one".

Column 32:
Line 35, delete "an".

Column 34:
Line 40, delete "IN" and insert --1N--.

Claim 1, line 47, change "halo alkyl" to --haloalkyl--.

Claim 3, line 7, change "loweralkyl" to --lower alkyl--.

Claim 8, line 4, after "yohimbine" insert --,--.

Claim 9, line 2, after "acetylcysteine" insert --,--.

UNITED STATES PATENT AND TRADEMARK OFFICE
CERTIFICATE OF CORRECTION

PATENT NO.   : 5,932,538
DATED        : August 3, 1999
INVENTOR(S)  : Garvey et al It is certified that error appears in the above-identified patent and that said Letters Patent is hereby corrected as shown below:

Claim 10, lines 6-7, change "$H_2N-(CO_2H)-(CH_s)_x-C(O)NH-C(CH_2SNO)-C(O)NH-CH_2$" to --$H_2N-CH(CO_2H)-(CH_2)_x-C(O)NH-CH(CH_2SNO)-C(O)NH-CH_2$--.
Line 26, change "halo alkyl" to --haloalkyl--.

Claim 14, line 5, change "13" to --N--.

Claim 15, line 4, change "compound to --composition--.

Signed and Sealed this

Seventh Day of August, 2001

*Attest:*

NICHOLAS P. GODICI
*Attesting Officer*    Acting Director of the United States Patent and Trademark Office